(12) United States Patent
Ekwuribe et al.

(10) Patent No.: US 8,143,366 B2
(45) Date of Patent: Mar. 27, 2012

(54) ARYL CARBAMATE OLIGOMERS FOR HYDROLYZABLE PRODRUGS AND PRODRUGS COMPRISING SAME

(75) Inventors: Nnochiri N. Ekwuribe, Cary, NC (US); Amy L. Odenbaugh, Cary, NC (US)

(73) Assignee: Biocon Limited (IN)

( * ) Notice: Subject to any disclaimer, the term of this patent is extended or adjusted under 35 U.S.C. 154(b) by 0 days.

(21) Appl. No.: 12/622,645

(22) Filed: Nov. 20, 2009

(65) Prior Publication Data

US 2010/0081782 A1    Apr. 1, 2010

Related U.S. Application Data

(62) Division of application No. 12/037,445, filed on Feb. 26, 2008, now Pat. No. 7,625,995, which is a division of application No. 10/525,290, filed as application No. PCT/US2004/015004 on May 6, 2004, now Pat. No. 7,335,751.

(60) Provisional application No. 60/491,751, filed on Aug. 1, 2003.

(51) Int. Cl.
- *C08G 63/06* (2006.01)
- *C08G 77/02* (2006.01)
- *C08G 65/40* (2006.01)

(52) U.S. Cl. ............ 528/208; 528/25; 528/86; 528/196; 528/205; 528/206; 525/219; 525/322; 525/391; 568/608

(58) Field of Classification Search .................. None
See application file for complete search history.

(56) References Cited

U.S. PATENT DOCUMENTS

| | | | |
|---|---|---|---|
| 4,145,342 | A | 3/1979 | Trautner et al. |
| 5,389,626 | A | 2/1995 | Kojima et al. |
| 5,413,614 | A | 5/1995 | Cherpeck et al. |
| 6,232,320 | B1 | 5/2001 | Stewart et al. |
| 6,413,507 | B1 | 7/2002 | Bentley et al. |
| 2002/0032303 | A1 | 3/2002 | Fulkuda et al. |
| 2006/0183832 | A1 | 8/2006 | Tsuchihashi et al. |

FOREIGN PATENT DOCUMENTS

| | | |
|---|---|---|
| DE | 2822191 | 11/1979 |
| EP | 0153642 | 9/1985 |
| EP | 0064876 | 8/1986 |
| EP | 0 400 486 A2 * | 12/1990 |
| JP | 51092831 | 8/1976 |
| JP | 57163596 | 10/1982 |
| JP | 05135769 | 6/1993 |
| JP | 10220133 | 4/1998 |
| WO | 98/38152 | 9/1989 |
| WO | 93/08196 | 4/1993 |
| WO | 95/29975 | 11/1995 |
| WO | 99/30727 | 6/1999 |
| WO | 02/102897 | 12/2002 |

OTHER PUBLICATIONS

Michael Roberts et al.; Molecule Engineering Including Advanced PEGylation: Understanding the Full Potential; The Drug Delivery Companies Report Spring/Summer 2003; pp. 19-21; USA.
Richard B. Greenwald et al.; Effective Drug Delivery by PEGylated Drug Conjugates; Advanced Drug Delivery Reviews; 2003; 55; pp. 217-250; Elsevier Science B.V.
Richard B. Greenwald et al.; Drug Delivery Systems Employing 1,4- or 1,6-Elimination: Poly(ethylene glycol) Prodrugs of Amine-Containing Compounds; J. of Medicinal Chemistry; 1999; vol. 42; pp. 3657-3667; American Chemical Society.
Ford, et al. (1992) Synthesis and Photochemical Properties of Aluminum, Gallium, Silicon, and Tin Naphthalocyanines, Inorg. Chem. 31, 3371-3377.
European Office Action, corresponding to European Patent Application No. 04752108.3, issued on Sep. 28, 2011.

\* cited by examiner

*Primary Examiner* — Rosalynd Keys
(74) *Attorney, Agent, or Firm* — Marianne Fuierer; Moore & Van Allen, PLLC

(57) ABSTRACT

The present invention provides a compound having a formula: where $R^1$ is selected from the group consisting of alkyl, $CH_2(OC_2H_4)OCH_3$, and $—(OC_2H_4)OCH_3$; n is 0-4; Olig is an oligomer having a formula:

-L-O-PAGR.$R^2$]$_q$ where L is a optional linker moiety selected from the group consisting of —$CH_2O$—, —$CH_2OX$—, —OX—, —C(O)—, —C(O)X, —NH—, —NHC(O)—, —XNHC(O)—, —NHC(O)X—, —C(O)NH—, —C(O)NHX—, and

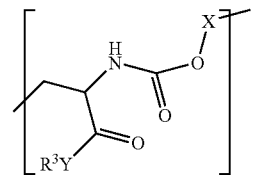

where X is alkyl$_{1-6}$ or is not present, Y is N or O or is not present, and $R^3$ is alkyl$_{1-6}$; PAG is a linear or branched polyalkylene glycol moiety; $R^2$ is an alkyl$_{1-22}$ capping moiety if X is present or alkyl$_{2-22}$ if X is not present; and q is a number from 1 to the maximum number of branches on PAG; and m is 1-5.

1 Claim, 4 Drawing Sheets

**Standard Curve for determination of
Conjugate 1 concentration for *in vitro* rat plasma study**

*Ex Vivo* Hydrolysis of Conjugate 1 in Rat Plasma at 37 °C

ARYL CARBAMATE OLIGOMERS FOR HYDROLYZABLE PRODRUGS AND PRODRUGS COMPRISING SAME

CROSS REFERENCE TO RELATED APPLICATIONS

This application is a divisional application of U.S. patent application Ser. No. 12/037,445 filed on Feb. 26, 2008, now U.S. Pat. No. 7,625,995, which in turn is a divisional application of U.S. patent application Ser. No. 10/525,290, filed on Jul. 18, 2005, now U.S. Pat. No. 7,335,751, which in turn is based on and claims priority to, International Patent Application No. PCT/US04/15004, filed May 6, 2004, and U.S. Provisional Patent Application No. 60/491,751, filed Aug. 1, 2003. The entire disclosure of each of these applications is incorporated here by reference in its entirety, and the benefit of the filing date of each such patent application is hereby claimed for all purposes that are legally served by such claim.

BACKGROUND OF THE INVENTION

1. Field of the Invention

The present invention relates to aryl carbamate oligomers for making hydrolyzable prodrugs, oligomerized prodrugs including such oligomers, methods of synthesizing the aryl carbamate oligomers and oligomerized prodrugs, and methods of treatment employing the use of such polymeric prodrugs.

2. Related Art

Many peptides and proteins (collectively referred to herein as "polypeptides") are potentially useful as therapeutic agents but lack an adequate means of administration. The usefulness of polypeptides as therapeutic agents is limited by the biological barriers that must be traversed before a polypeptide can reach its specific in vivo target. Parenterally administered polypeptides are readily metabolized by plasma proteases. Oral administration, which is perhaps the most attractive route of administration, is even more problematic. In the stomach, acid degrades and enzymes break down proteins. Those polypeptides that survive to enter the intestine intact are subjected to additional proteolysis as they are continuously barraged by a variety of enzymes, including gastric and pancreatic enzymes, exo- and endopeptidases, and brush border peptidases. As a result, passage of polypeptides from the lumen of the intestine into the bloodstream is severely limited. There is, therefore, a need in the art for means which enable parenteral and oral administration of therapeutic polypeptides.

Various strategies have been used in attempts to improve oral and parenteral delivery of polypeptides. Some of the approaches used include the use of enzyme inhibitors to slow the rate of degradation of proteins and peptides in the gastrointestinal tract; manipulation of pH to inactivate local digestive enzymes; use of permeation enhancers to improve the absorption of protein and peptides by increasing their paracellular and transcellular transports; use of nanoparticles as particulate carriers to facilitate intact absorption by the intestinal epithelium, especially, Peyer's patches, and to increase resistance to enzyme degradation; liquid emulsions to protect the drug from chemical and enzymatic breakdown in the intestinal lumen; and micelle formulations for poorly water solubilized drugs.

An important subset of the strategies for improving administration of polypeptides has been the conjugation of polypeptides to various moieties, such as polymeric moieties, to modify the physiochemical properties of polypeptide drugs to increase resistance to acidic and enzymatic degradation and to enhance penetration of such drugs across mucosal membranes. For example, Abuchowski and Davis have described various methods for derivatizating enzymes to provide water-soluble, non-immunogenic, in vivo stabilized products ("Soluble polymers-Enzyme adducts", Enzymes as Drugs, Eds. Holcenberg and Roberts, J. Wiley and Sons, New York, N.Y., (1981)). Abuchowski and Davis discuss various ways of conjugating enzymes with polymeric materials, such as dextrans, polyvinyl pyrrolidones, glycopeptides, polyethylene glycol and polyamino acids. The resulting conjugated polypeptides are reported to retain their biological activities and solubility in water for parenteral applications. Furthermore, in U.S. Pat. No. 4,179,337, Davis et al. report that polypeptides, such as enzymes and insulin, can be coupled to polyethylene glycol or polypropropylene glycol having a molecular weight of 500 to 20,000 daltons to provide a physiologically active non-immunogenic water soluble polypeptide composition. The polyethylene glycol or polypropylene glycol is reported to protect the polypeptide from loss of activity and the composition can be injected into the mammalian circulatory system with substantially no immunogenic response. However, this approach is directed towards improving parenteral administration of polypeptides, not oral delivery.

Other researchers have shown that polyethylene glycol linked to a protein improves stability against denaturation and enzymatic digestion. (Boccu et al. Pharmacological Research Communication 14, 11-120 (1982)). However, these polymers do not contain components for enhancing membrane interaction. Thus, the resulting conjugates suffer from the same problems as noted above and are not suitable for oral administration.

Our own prior work involving the conjugation of polypeptides to amphiphilic oligomers, i.e., oligomers having hydrophilic and lipophilic characteristics, has been a major advance in the field of oral delivery of polypeptides. For example, U.S. Pat. No. 5,681,811 to Ekwuribe et al., and related U.S. Pat. Nos. 5,438,040 and 5,359,030, describe stabilized, conjugated polypeptide complexes including a therapeutic agent coupled to an oligomer that includes lipophilic and hydrophilic moieties. A preferred subset of the polypeptide-oligomer conjugates described in the '811 patent includes a polymer having a linear polyalkylene glycol moiety and a linear alkyl moiety.

U.S. Pat. No. 6,309,633 to Ekwuribe et al. describes a "partial prodrug" approach in which a polypeptide is conjugated to an oligomer having hydrophilic and lipophilic components, and the lipophilic component is hydrolyzable under physiological conditions. Conjugation of a polypeptide using the oligomers results in a "partial prodrug" in which the presence of the full oligomer assists in delivering the orally administered conjugate through the digestive tract into the bloodstream where the lipophilic component is hydrolyzed to leave the hydrophilic component (e.g., polyethylene glycol polymer). Hydrolysis of the lipophilic component in the bloodstream can render the conjugate bioactive (or improve bioactivity) and/or improve circulation half-life. However, there remains a significant need in the art for a means of amphiphilically conjugating polypeptides for oral delivery in a manner which does not eliminate useful bioactivity of the parent polypeptide.

Prodrug approaches are commonly used with small molecule therapeutics. For example, patented 6-MNA and paclitaxel prodrugs are known to make use of ester prodrugs of carboxylates and alcohols, while the APAZA™ compound (Nobex Corporation, Research Triangle Park, N.C.) is a prodrug in which two independently active small molecule drugs are bonded together by an azo linkage that is reductively cleaved in vivo (See U.S. Pat. Nos. 6,552,078, 6,541,508, 6,525,098, 6,436,990 and 6,380,405).

Garmen et al. describe a protein-PEG prodrug (Garman, A. J., and Kalindjian, S. B., *FEBS Lett.*, 1987, 223, 361-365). The authors report the preparation of a maleic anhydride reagent from polydispersed MPEG5000 and conjugation to tissue plasminogen activator and urokinase. The reaction of amino acids with maleic anhydrides is commonly used in peptide sequencing chemistry. The hydrolysis of the maleyl-amide bond to reform the amine-containing drug is aided by the presence of the neighboring free carboxyl group and the geometry of attack set up by the double bond. Garman states that the native proteins of the maleic anhydride conjugates were released under physiological conditions, and administration via a prodrug increased clearance rates for the proteins by five to ten times.

More recently, in the development of a pegylated interferon, Roberts et al. have described the use of a degradable linkage between polydispersed PEG and interferon α-2b (Roberts, M. J. et al., *Adv. Drug Delivery Rev.*, 2002, 54, 459-476). The authors reported that conjugating PEG to interferon at low pH (~5) resulted in conjugates that were linked through a carbamate to one of the nitrogens of the imidazole ring of histidine. Over time, PEG was released from the protein. These PEG-interferon α-2b conjugates are known by the trade name of PEG-Intron® (Schering Corporation). While in vitro PEG-Intron® is reported to be more active than PEGASYS® (pegylated interferon with a non-hydrolyzable branched PEG, Hoffmann-La Roche), PEGASYS® is reported to be more efficacious in vivo.

Other efforts in the area of releasable PEG chemistry have focused on using 1, 6 or 1,4 benzyl elimination (BE) strategies (Lee, S., et al., Bioconjugate Chem., 2001, 12, 163-169; Greenwald, R. B. et al., U.S. Pat. No. 6,180,095, 2001; Greenwald, R. B., et al., J. Med. Chem., 1999, 42, 3657-3667.); the use of trimethyl lock lactonization (TML) (Greenwald, R. B. et al., J. Med. Chem., 2000, 43, 475-487); the coupling of PEG carboxylic acid to a hydroxy-terminated carboxylic acid linker (Roberts, M. J., J. Pharm. Sci., 1998, 87(11), 1440-1445), and PEG prodrugs involving families of MPEG phenyl ethers and MPEG benzamides linked to an amine-containing drug via an aryl carbamate (Roberts, M. J., et al., Adv. Drug Delivery Rev., 2002, 54, 459-476), including a prodrug structure involving a meta relationship between the carbamate and the PEG amide or ether (U.S. Pat. No. 6,413,507 to Bently et al.); and prodrugs involving a disulfide reduction mechanism as opposed to a hydrolysis mechanism (Zalipsky, S., et al., Bioconjugate Chem., 1999, 10(5), 703-707).

The present invention provides further developments regarding a prodrug approach in which a protein-oligomer prodrug is delivered through the digestive tract and into the bloodstream where the oligomer portion is released to yield the fully active protein.

SUMMARY OF THE INVENTION

The present invention can provide a "pure prodrug" approach to polypeptide conjugation in which at least a portion of orally administered prodrug (i) remains in prodrug form (i.e., the oligomer remains attached), protecting the polypeptide through the digestive tract; (ii) traverses the wall of the digestive tract and enters into the blood stream; and/or (iii) converted in the system (e.g., in the bloodstream and/or in the liver) to yield the fully bioactive parent polypeptide in a therapeutically effective amount.

According to embodiments of the present invention, a compound is provided that has the formula:

(Formula 1)

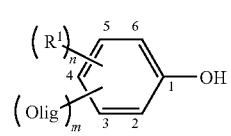

where
$R^1$ is alkyl, —$CH_2(OC_2H_4)OCH_3$, and —$(OC_2H_4)OCH_3$;
n is 0-4;
Olig is an oligomer having a formula:

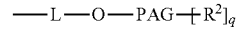

where:
L is a optional linker moiety selected from the group consisting of —$CH_2O$—, —$CH_2OX$—, —OX—, —C(O)—, —C(O)X—, —NH—, —NHC(O)—, —XNHC(O)—, —NHC(O)X—,
—C(O)NH—, —C(O)NHX—, and

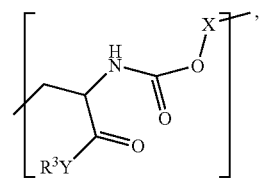

where:
X is alkyl$_{1-6}$ or is not present,
Y is N or O or is not present, and
$R^3$ is alkyl$_{1-6}$,
PAG is a linear or branched polyalkylene glycol moiety;
$R^2$ is an alkyl$_{1-22}$ capping moiety if X is present or alkyl$_{2-22}$ if X is not present; and
q is a number from 1 to the maximum number of branches on PAG; and
m is 1-5.

In other embodiments, the invention provides pure prodrugs and partial prodrugs comprising compounds of Formula I, pharmaceutical compositions including the compounds of the present invention, methods of synthesizing such compounds, methods of treating a subject in need of treatment utilizing such compounds, and use of the compounds of the present invention for the preparation of a medicament.

BRIEF DESCRIPTION OF THE DRAWINGS

(FIG. 2B).

DETAILED DESCRIPTION OF THE INVENTION

Definitions

Figure 1A:
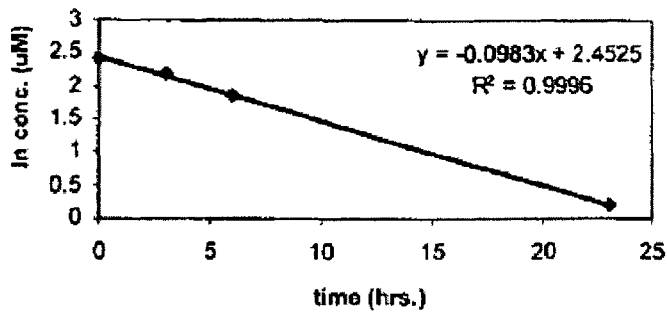
FIGS. 1A-G illustrate graphs depicting esterase hydrolysis of Leu-Enk conjugated prodrugs of the present invention. The pseudo first-order rate constant was obtained from the slope of the ln conjugate conc. (μM) versus time (min.) curve for each conjugate. The half-life of the conjugates was also obtained.
Figure 1B:
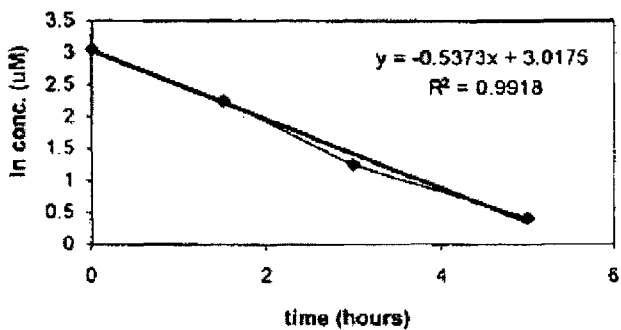
Figure 1C:
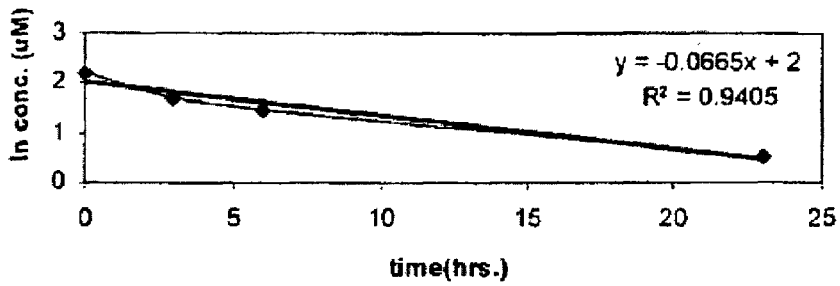
Figure 1D:
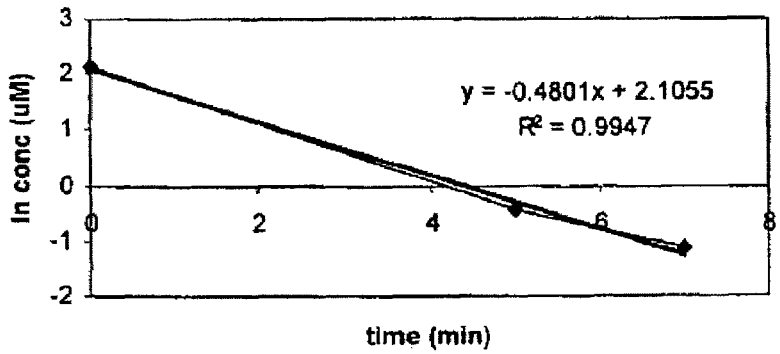
Figure 1E:
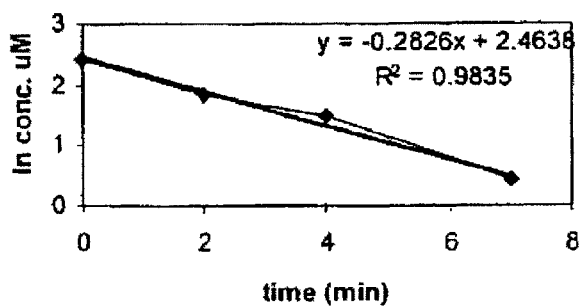
Figure 1F:
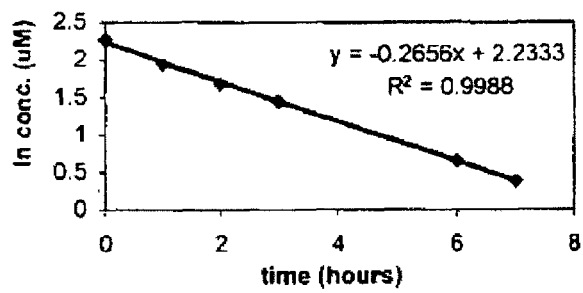
Figure 1G:
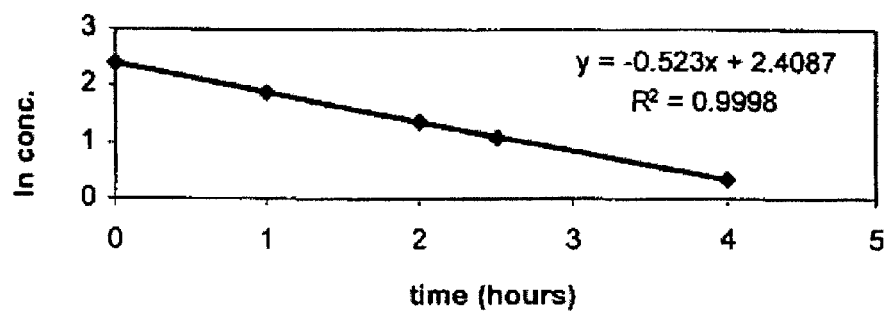

The terminology used in the description of the invention is for the purpose of describing particular embodiments only and is not intended to be limiting of the invention. As used in the description of the invention and the claims, the singular forms "a," "an," and "the" are intended to include the plural forms as well, unless the context clearly indicates otherwise.

As used herein, the following terms have the meanings indicated:

"Prodrug" or "pure prodrug" means a biologically active agent that has been chemically derivitized such that, (i) it retains some, all or none of the bioactivity of its parent drug compound, and (ii) it is metabolized in a subject to yield the parent drug compound. In the context of an oligomerized polypeptide prodrug or pure prodrug, the entire oligomer can be removed in vivo to yield the biologically active unconjugated polypeptide.

"Partial prodrug" means a biologically active agent that has been chemically derivitized such that, (i) it retains some, all or none of the bioactivity of its parent drug compound, and (ii) it is metabolized in a subject to yield a biologically active derivative of the biologically active agent. In the context of a oligomerized polypeptide partial prodrug, a biologically active peptide derivative (e.g., a polymer-conjugated and/or oligomer-conjugated polypeptide) can be produced in vivo by cleavage of a portion of one or more oligomers and/or cleavage of one or more complete oligomers.

"Biologically active agent" means a therapeutic or pharmacologic agent that can be conjugatable in the manner of the present invention. A biologically active agent can be a small molecule, peptide, or protein. Examples of biologically active agents include, but are not limited to, those falling into the following therapeutic categories: ACE-inhibitors; anti-anginal drugs; anti-arrhythmias; anti-asthmatics; anti-cholesterolemics; anti-convulsants; anti-depressants; anti-diarrhea preparations; anti-histamines; anti-hypertensive drugs; anti-infectives; anti-inflammatory agents; anti-lipid agents; anti-manics; anti-nauseants; anti-stroke agents; anti-thyroid preparations; anti-tumor drugs; anti-tussives; anti-uricemic drugs; anti-viral agents; acne drugs; alkaloids; amino acid preparations; anabolic drugs; analgesics; anesthetics; angiogenesis inhibitors; antacids; anti-arthritics; antibiotics; anticoagulants; antiemetics; antiobesity drugs; antiparasitics; antipsychotics; antipyretics; antispasmodics; antithrombotic drugs; anxiolytic agents; appetite stimulants; appetite suppressants; beta blocking agents; bronchodilators; cardiovascular agents; cerebral dilators; chelating agents; cholecystokinin antagonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypnotics; hypoglycemic agents; laxatives; migraine treatments; mineral supplements; mucolytics; narcotics; neuroleptics; neuromuscular drugs; NSAIDS; nutritional additives; peripheral vasodilators; prostaglandins; psychotropics; renin inhibitors; respiratory stimulants; steroids; stimulants; sympatholytics; thyroid preparations; tranquilizers; uterine relaxants; vaginal preparations; vasoconstrictors; vasodilators; vertigo agents; vitamins; and wound healing agents. Other non-limiting examples of biological agents include coumarin, insulin, calcitonin, leu-enkaphalin, and met-enkaphalin.

"Hydrolyzable" means bonds that can be hydrolyzed under physiological conditions.

"Solubility" refers to the tendency of one substance to blend uniformly with another.

"Hydrophilic" means the ability to dissolve in water; "hydrophilic moiety" or "hydrophile" refers to a moiety which is hydrophilic and/or which when attached to another chemical entity, increases the hydrophilicity of such chemical entity.

"Lipophilic" means the ability to dissolve in lipids and/or the ability to penetrate, interact with and/or traverse biological membranes; "lipophilic moiety" or "lipophile" means a moiety which is lipophilic and/or which, when attached to another chemical entity, increases the lipophilicity of such chemical entity.

"Amphiphilic" means the characteristic of exhibiting both water solubility and fat solubility.

"Polyalkylene glycol" means straight or branched polyalkylene glycol polymers including, but not limited to, polyethylene glycol, polypropylene glycol, and polybutylene glycol, and includes the monoalkylether of the polyalkylene glycol. In one embodiment, the polyalkylene glycol is polyethylene glycol or "PEG". The term "PEG subunit" refers to a single polyethylene glycol unit, i.e., —($CH_2CH_2O$)—. Additionally, the term "oligomer" can be used to refer to a polymer.

"Monodispersed" is used to describe a mixture of compounds wherein about 100 percent of the compounds in the mixture have the same molecular weight.

"Substantially monodispersed" is used to describe a mixture of compounds wherein at least about 95 percent of the compounds in the mixture have the same molecular weight.

"Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture.

"Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture.

"Weight average molecular weight" is defined as the sum of the products of the weight fraction for a given molecule in the mixture times the mass of the molecule for each molecule in the mixture. The "weight average molecular weight" is represented by the symbol $M_w$.

"Number average molecular weight" is defined as the total weight of a mixture divided by the number of molecules in the mixture and is represented by the symbol $M_n$.

"Dispersity coefficient" (DC) is defined by the formula:

$$DC = \frac{\left(\sum_{i=1}^{n} N_i M_i\right)^2}{\sum_{i=1}^{n} N_i M_i^2 \sum_{i=1}^{n} N_i - \left(\sum_{i=1}^{n} N_i M_i\right)^2}$$

wherein:
n is the number of different molecules in the sample;
$N_i$ is the number of $i^{th}$ molecules in the sample; and
$M_i$ is the mass of the $i^{th}$ molecule.

"Chemical stability" refers to the stability of a given compound in physiological or pseudo-physiological environments. For example, chemical stability refers to the stability of the biologically active agent or prodrug in environments characterized by conditions such as, but not limited to, the presence of plasma, the presence of proteases, the presence of liver homogenate, the presence of acidic conditions, and the presence of basic conditions.

"Effective amount" refers to an amount of a compound or composition that is sufficient to produce a desired effect, which can be a therapeutic effect. The effective amount can vary with the age, general condition of the subject, the severity of the condition being treated, the particular biologically active agent administered, the duration of the treatment, the nature of any concurrent treatment, the pharmaceutically acceptable carrier used, and like factors within the knowledge and expertise of those skilled in the art. An "effective amount" in any individual case can be determined by one of ordinary skill in the art by reference to the pertinent texts and literature and/or by using routine experimentation. (See, for example, Remington, *The Science And Practice of Pharmacy* (20th ed. 2000).

A "pharmaceutically acceptable" component such as a salt, carrier, excipient or diluent of a composition according to the present invention is a component that (i) is compatible with the other ingredients of the composition in that it can be combined with the prodrugs of the present invention without rendering the prodrug unsuitable for its intended purpose, and/or (ii) is suitable for use with subjects as provided herein without undue adverse side effects (such as toxicity, irritation, and allergic response). Side effects are "undue" when their risk outweighs the benefit provided by the pharmaceutical composition. Non-limiting examples of pharmaceutically acceptable components include, without limitation, any of the standard pharmaceutical carriers such as phosphate buffered saline solutions, water, emulsions such as oil/water emulsion, microemulsions and various types of wetting agents.

"Treat" or "treating" refers to any type of treatment that imparts a modulating effect, which, for example, can be a beneficial effect to a subject afflicted with a disorder, disease or illness, including improvement in the condition of the subject (e.g., in one or more symptoms), delay in the progression of the condition, and/or prevention or delay of the onset of the disorder, change in clinical parameters, disease or illness, etc.

The invention provides an aryl carbamate class of oligomers for conjugation to biologically active agents, such as drug moieties, and especially protein drug moieties. When conjugated, the oligomers yield orally bioavailable pure prodrugs that hydrolyze in vivo to yield the biologically active parent compound.

Oligomers of the Invention

In general, the oligomers of the invention have the following formula:

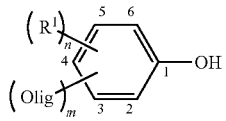
(Formula 1)

where
each $R^1$ may be the same or different and each is selected from the group consisting of alkyl, —$CH_2(OC_2H_4)OCH_3$, and —$(OC_2H_4)OCH_3$;
n is 0-4;
each Olig may be the same or different and each is an oligomer having a formula:

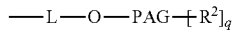

where:
L is a optional linker moiety selected from the group consisting of —$CH_2O$—, —$CH_2OX$—, —OX—, —C(O)—, —C(O)X, —NH—, —NHC(O)—, —XNHC(O)—, —NHC(O)X—, —C(O)NH—, —C(O)NHX—, and

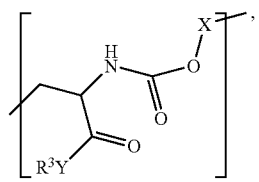

where:
X is alkyl$_{1-6}$ or is not present,
Y is N or O or is not present, and
$R^3$ is alkyl$_{1-6}$;
PAG is a linear or branched polyalkylene glycol moiety;
each $R^2$ may be the same or different and is selected from the group consisting of alkyl$_{1-22}$ capping moieties if X is present and alkyl$_{2-22}$ if X is not present; and
q is a number from 1 to the maximum number of branches on PAG; and
m is 1-5.

In Formula 1, one or more Oligs may be present. Each Olig is coupled at any of carbons 2 to 5 of the phenol moiety of Formula 1. For example, in one embodiment, an Olig is coupled to carbon 4 of the phenol moiety. In another embodiment, an Olig is coupled to carbon 4 of the phenol moiety and one or more Oligs is coupled to other carbons in addition to carbon 4. In some embodiments, a single Olig (i.e., m=1) is coupled to carbon 4 of the phenol moiety. In other exemplary embodiments, an Olig is coupled to carbon 3 of the phenol moiety, and/or an Olig is coupled to carbon 5 of the phenol moiety. In yet another embodiment, two Oligs (i.e., m=2) are coupled to carbons 3 and 5 of the phenol moiety.

In some embodiments, L is present and X is not present. In other embodiments, both L and X are present.

PAG may be a linear or branched polyalkylene glycol moiety. Preferred polyalkylene glycol moieties include linear or branched polyethylene glycol and linear or branched polypropylene glycol. In a some embodiments, the polyethylene glycol or polypropylene glycol is non-polydispersed, monodispersed, substantially monodispersed, purely monodispersed, or substantially purely monodispersed, as these terms are described in U.S. patent application Ser. No. 09/873,797, filed Jun. 4, 2001, the entire disclosure of which is incorporated herein by reference.

In one embodiment, $R^2$ is an $alkyl_{1-22}$ capping moiety if X is present or $alkyl_{2-22}$ if X is not present. $R^2$ is suitably $alkyl_{1-22}$, preferably $alkyl_{1-12}$, and more preferably $alkyl_{1-6}$. $R^2$ is suitably an alkyl moiety having a number of carbons ranging from a lower limit of 1, 2, 3, 4, 5, 6, 7, 8, 9, 10, 11, 12, 13, 14, 15, 16, 17, 18, 19, 20, or 21 to an upper limit of 2, 3, 4, 5, 6, 7, 8, 9, 10, 11, 12, 13, 14, 15, 16, 17, 18, 19, 20, 21 or 22, in any combination of ranges satisfying the condition that the lower limit is less than the upper limit (lower limit<upper limit). In a specific embodiment, when X is present, $R^2$ is methyl.

If the PAG moiety is branched, then the number q of $R^2$ moieties present in the oligomer is limited to the number of branches on the branched PAG. For example, q may be suitably 1, 2, 3, 4, 5, 6, 7, 8, 9 or 10. In some embodiments PAG has 2, 3, 4, or 5 branches, and q is respectively 2, 3, 4 or 5. In another embodiment, PAG has 2 branches and q is 2. Where q is greater than 1, each instance of $R^2$ may be the same or may be different. For example, if q is 3, 2 instances of $R^2$ may be $C_2$ and one may be $C_7$.

In one embodiment, $R^1$ is methyl. In another embodiment, $R^1$ is methyl and L is not amide or O.

The invention also provides an activated form of any of the foregoing oligomers, e.g., a chloroformate, NHS carbonate, or paranitrophenyl carbonate of any of the foregoing oligomers. In general, the compound having the reactive moiety is contacted with an activating agent in a suitable solvent, for a suitable amount of time, at a suitable temperature as will be understood by those skilled in the art. For example, the oligomer may be reacted with DSC para-nitrochloroformate or phosgene to activate.

The invention also provides a prodrug including a parent compound covalently coupled to one or more of the foregoing oligomers by a carbamate bond. In an embodiment, the parent compound is a polypeptide drug.

Other oligomers of the invention include the oligomers of Formulas 2-10, shown below. In these oligomers, X can be an alkyl, as indicated. The alkyl may be linear or branched and may, for example, include 2, 3, 4, 5, 6, 7, 8, 9, 10, 11, 12, 13, 14, 15, 16, 17, 18, 19, 20, 21, or 22 carbon atoms. PEG in any of Formulae 2-10 can be a linear or branched polyethylene glycol moiety, and may, for example, include 1-50 PEG units, 2-25 PEG units, 2-12 PEG units. PEG may have 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 PEG units. R in any of Formulae 2-10 is suitably $alkyl_{1-22}$, preferably $alkyl_{1-12}$, and more preferably $alkyl_{1-6}$. R is suitably an alkyl moiety having 1, 2, 3, 4, 5, 6, 7, 8, 9, 10, 11, 12, 13, 14, 15, 16, 17, 18, 19, 20, 21 or 22 carbon units. It will be appreciated that the PEG in Formulae 2-10 may readily be replaced with a PAG, such as PPG.

Oligomers of Formula 2 are based on hydroquinone, and have the following formula:

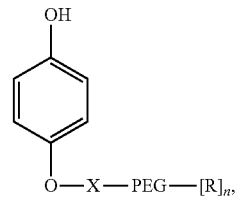

(Formula 2)

wherein
X is an alkyl;
PEG is linear or branched $PEG_{2-50}$,
R is H or alkyl; and
n is a number from 1 to the maximum number of PEG branches.

Oligomers of Formula 3 are based on p-hydroxybenzyl alcohol:

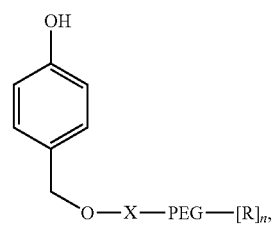

(Formula 3)

wherein
X is an alkyl or is not present;
PEG is linear or branched $PEG_{2-50}$,
R is H or alkyl; and
n is a number from 1 to the maximum number of PEG branches.

Given the large number of suitable starting materials (e.g., hydroquinones and p-hydroxy benzyl alcohol) that are commercially available for compounds of Formulae 1 and 2, these strategies can benefit from a wide variety of other substituents present on the aromatic ring. Addition of electron-donating groups (e.g., ether, amino or alkyl groups) or electron-withdrawing groups (e.g., nitro or carboxyl groups) or addition of steric bulk moieties (e.g., alkyl groups) ortho to the oxygen of the hydroxyl moiety (the eventual carbamate moiety) can aid in fine-tuning drug release.

Carbamate oligomers of Formula 4 illustrate an approach in which the benzyl ether has added groups ortho to the phenol that will become the oxygen in the carbamate of the prodrug:

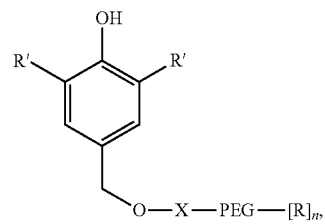

wherein
X is an alkyl or is not present;
PEG is linear or branched $PEG_{2-50}$;
R is H or alkyl;

R' is alkyl; and n is a number from 1 to the maximum number of PEG branches.

Use of methyl groups at the R' substituents can be used to partially block esterase activity and slow prodrug hydrolysis. Use of bulkier groups, such as t-butyl groups, can be used to slow hydrolysis further.

Carbamate oligomers of the Formulae 5 and 6 illustrate how the strategies employed with Formulae 2 and 3 may be altered to provide a branched hydrolyzable oligomer. Thus, the invention provides:

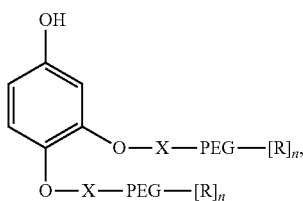
(Formula 5)

wherein
X is an alkyl or is not present;
PEG is linear or branched $PEG_{2-50}$,
R is H or alkyl; and
n is a number from 1 to the maximum number of PEG branches.

The invention also provides an oligomer having a formula:

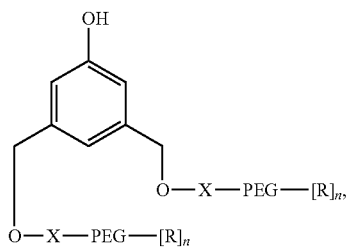
(Formula 6)

wherein
X is an alkyl or is not present;
PEG is linear or branched $PEG_{2-50}$,
R is H or alkyl; and
n is a number from 1 to the maximum number of PEG branches.

Formulae 7, 8, and 9 illustrate approaches in which the linkage of the PEG to the aryl ring involves the use of an electron-withdrawing amide (Formulae 7 and 8) or ketone (Formula 9) groups. Thus, the invention provides:

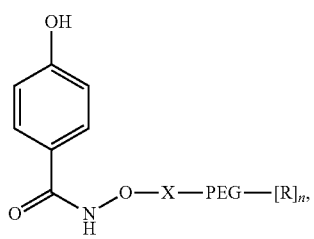
(Formula 7)

wherein
X is an alkyl or is not present;
PEG is linear or branched $PEG_{2-50}$,
R is H or alkyl and
n is a number from 1 to the maximum number of PEG branches.

The invention also provides:

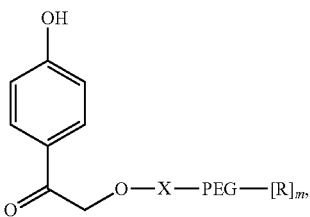
(Formula 8)

wherein
X is an alkyl or is not present;
n is 1-22;
PEG is linear or branched $PEG_{2-50}$;
R is H or alkyl; and
m is a number from 1 to the maximum number of PEG branches.

The invention also provides an oligomer having a formula:

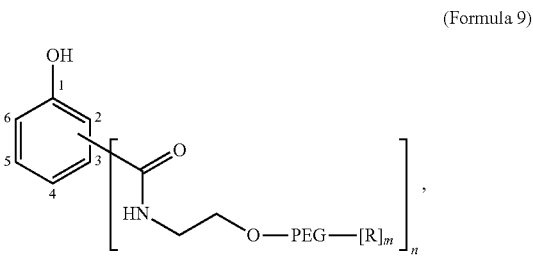
(Formula 9)

wherein
PEG is linear or branched $PEG_{2-50}$, and
R is H or alkyl;
n is 1 or 2 or 3; and
m is a number from 1 to the maximum number of PEG branches.

In an embodiment of the oligomer of Formula 9, n is 2 and

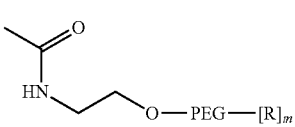

is bound to the phenol moiety at positions 3 and 4.

The invention also provides an oligomer having a formula:

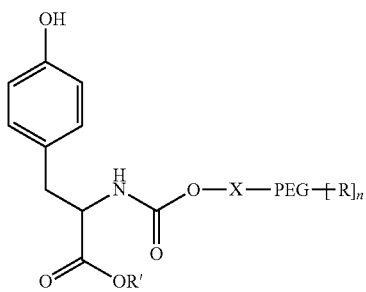

(Formula 10)

wherein
X is alkyl or is not present;
PEG is linear or branched $PEG_{2-50}$;
R is H or alkyl;
n is from 1 to the maximum number of PEG branches; and
$R^1$ is alkyl.

Carbamate oligomers of Formula 10 are based on the structure of the amino acid tyrosine, a molecule that is readily available in a number of partially protected forms. Oligomers of Formula 10 have three potentially hydrolyzable bonds in vivo and could regenerate the amino acid.

It should be further noted that any substituent can be excluded from a particular compound.

Oligomer Synthesis

Various synthetic routes to oligomers of the invention are illustrated in the Examples set forth herein. It will be appreciated that one of skill in the art can readily extrapolate from these examples to produce a wide variety of oligomers according to the invention.

Prodrugs of the Invention

Conjugation of the biologically active agent with a hydrolyzable oligomer moiety of the invention may result in a pure prodrug having improved chemical stability relative to the parent bioactive moiety, e.g., improved stability in the presence of proteases or other enzymes relative to the parent bioactive moiety. Various attributes of chemical stability can be assessed by exposing the prodrug to various assay conditions such as the presence of plasma, the presence of proteases, the presence of liver homogenate, the presence of acidic conditions, and the presence of basic conditions. Stability is improved relative to the parent compound when stability of the prodrug in any one or more of these assay conditions is greater than stability of the parent compound in the same conditions. An assay for determining chemical stability in an acidic environment involves exposing the prodrug and parent drug compound to a solution having a pH of 2 for at least 2 hours, wherein decreased degradation of the prodrug relative to the parent drug compound is indicative of improved chemical stability.

In vivo assays can also be used to test chemical stability. For example, chemical stability of the biologically active agent or prodrug can be tested by exposure to the gastrointestinal tract of a subject.

Conjugation of the biologically active agent with an oligomer of the invention will also, in some cases, improve the solubility of the biologically active agent resulting in the prodrug having improved aqueous solubility relative to the parent agent. In other cases, conjugation of the biologically active agent with an oligomer of the invention will render the agent more lipophilic and better able to traverse biological membranes relative to the parent agent.

Prodrug Synthesis

According to embodiments of the present invention, a process for synthesizing a prodrug having a hydrolyzable moiety includes contacting a biologically active agent with a compound comprising an oligomer moiety of the invention. Either the biologically active agent or the compound comprising the polymer moiety may be activated using various reactions known in the art such that the biologically active agent reacts with the compound comprising the polymer moiety to form a hydrolyzable bond to provide a prodrug having a hydrolyzable moiety. The polymer moiety can affect the chemical stability of the biologically active agent such that the prodrug exhibits a level of chemical stability greater than or equal to the chemical stability of the unconjugated biologically active agent, e.g., improved stability in the presence of proteases or other enzymes relative to the parent bioactive moiety. As discussed above, the polymer moiety may also positively effect solubility and absorbability by making the resulting conjugate more or less soluble, depending on the particular needs of the compound.

Those skilled in the art will readily understand the conditions sufficient for providing the activated compound. In general, the compound having the reactive moiety is contacted with the activating agent in a suitable solvent, for a suitable amount of time, at a suitable temperature as will be understood by those skilled in the art. For example, the compound may be reacted with DSC or para-nitrochloroformate or phosgene to activate.

Those skilled in the art will understand the conditions sufficient to couple the biologically active agent with the activated compound comprising a polymer moiety to provide a prodrug having a hydrolyzable moiety. In general, the biologically active agent is contacted with the activated compound comprising a polymer moiety in the presence of a suitable solvent. A suitable solvent will be one that can solubilize the biologically active agent and the compound comprising a polymer moiety to an extent that allows the compounds to react with one another. Suitable solvents include, but are not limited to, buffered aqueous solutions and organic solvents. Non-limiting examples of such organic solvents include $C_1$-$C_4$ alcohols such as methanol, ethanol, 1-propanol, 2-propanol, and butanol, as well as solvents such as acetone, tetrahydrofuran, acetonitrile, dimethyl formamide and dimethylsulfoxide.

The biologically active agent and the activated compound comprising a polymer moiety are preferably contacted for an amount of time and under conditions sufficient to provide a desirable yield of the prodrug.

Variations on the disclosed general synthetic methods will be readily apparent to those of ordinary skill in the art and are deemed to be within the scope of the present invention.

In some embodiments of the present invention, the prodrug is provided as a pharmaceutically acceptable salt. Pharmaceutically acceptable salts are salts that can retain the desired biological activity of the parent compound and generally do not impart undesired toxicological effects. Examples of such salts are acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like. In some embodiments, the pharmaceutically acceptable salt is formed with hydrochloric acid (or acetic acid).

Pharmaceutical Compositions

According to still other embodiments of the present invention, a pharmaceutical composition comprising a prodrug as described above is provided. In the manufacture of a pharmaceutical composition according to embodiments of the present invention, the prodrug is typically admixed with, inter alia, a pharmaceutically acceptable carrier. The carrier must, of course, be acceptable in the sense of being compatible with any other ingredients in the pharmaceutical composition and should not be deleterious to the patient. The carrier may be a solid or a liquid, or both, and can be formulated with the prodrug as a unit-dose formulation, for example, a tablet, which may contain from about 0.01 or 0.5% to about 95% or 99% by weight of the prodrug. The pharmaceutical compositions may be prepared by any of the well-known techniques of pharmacy including, but not limited to, admixing the components, optionally including one or more accessory ingredients.

The pharmaceutical compositions according to embodiments of the present invention include those suitable for oral, rectal, topical, inhalation (e.g., via an aerosol) buccal (e.g., sub-lingual), vaginal, parenteral (e.g., subcutaneous, intramuscular, intradermal, intraarticular, intrapleural, intraperitoneal, intracerebral, intraarterial, or intravenous), topical (i.e., both skin and mucosal surfaces, including airway surfaces) and transdermal administration, although the most suitable route in any given case will depend on the nature and severity of the condition being treated and on the nature of the particular prodrug which is being used.

Pharmaceutical compositions suitable for oral administration may be presented in discrete units, such as capsules, cachets, lozenges, or tables, each containing a predetermined amount of the prodrug; as a powder or granules; as a solution or a suspension in an aqueous or non-aqueous liquid; or as an oil-in-water or water-in-oil emulsion. Such formulations may be prepared by any suitable method of pharmacy that includes the step of bringing into association the prodrug and a suitable carrier (which may contain one or more accessory ingredients as noted above). In general, the pharmaceutical composition according to embodiments of the present invention can be prepared by uniformly and intimately admixing the prodrug with a liquid or finely divided solid carrier, or both, and then, if necessary, shaping the resulting mixture. For example, a tablet may be prepared by compressing or molding a powder or granules containing the prodrug, optionally with one or more accessory ingredients. Compressed tablets may be prepared by compressing, in a suitable machine, the mixture in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions suitable for buccal (sub-lingual) administration include lozenges comprising the prodrug in a flavored base, usually sucrose and acacia or tragacanth; and pastilles comprising the prodrug in an inert base such as gelatin and glycerin or sucrose and acacia.

Pharmaceutical compositions according to embodiments of the present invention suitable for parenteral administration comprise sterile aqueous and non-aqueous injection solutions of the prodrug, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The compositions may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, an injectable, stable, sterile composition comprising a prodrug in a unit dosage form in a sealed container may be provided. The prodrug is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the prodrug. When the prodrug is substantially water-insoluble, a sufficient amount of emulsifying agent which is physiologically acceptable may be employed in sufficient quantity to emulsify the prodrug in an aqueous carrier. One such useful emulsifying agent is phosphatidyl choline.

Pharmaceutical compositions suitable for rectal administration are preferably presented as unit dose suppositories. These may be prepared by admixing the prodrug with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which may be used include petroleum jelly, lanolin, polyethylene glycols, alcohols, transdermal enhancers, and combinations of two or more thereof.

Pharmaceutical compositions suitable for transdermal administration may be presented as discrete patches adapted to remain in intimate contact with the epidermis of the recipient for a prolonged period of time. Compositions suitable for transdermal administration may also be delivered by iontophoresis (see, for example, *Pharmaceutical Research* 3 (6): 318 (1986)) and typically take the form of an optionally buffered aqueous solution of the prodrug. Suitable formulations comprise citrate or TRIS buffer (pH 6) or ethanol/water and contain from 0.1 to 0.2M active ingredient.

Methods of Treatment

According to other embodiments of the present invention, methods of treating a subject in need of such treatment include administering an effective amount of a composition of this invention to the subject. The effective amount can vary somewhat from composition to composition, and subject to subject, and will depend upon factors such as the age, species, gender and/or condition of the subject and the route and mode of delivery. Such dosages can be determined in accordance with routine pharmacological procedures known to those skilled in the art. As a general proposition, a dosage from about 100 µg/kg to about 100 mg/kg will have efficacy, with all weights being calculated based upon the weight of the composition and/or active ingredient (e.g., prodrug). A dosage from about 10 mg/kg to about 50 mg/kg may be employed for oral administration. Typically, a dosage from about 0.5 mg/kg to 5 mg/kg may be employed for intramuscular injection. The frequency of administration can be one, two, or three times per day/week/month/year or as necessary to treat the condition. The duration of treatment depends on the type of condition being treated and can be for as long as the life of the patient.

Subjects suitable to be treated according to the present invention include, but are not limited to, avian and mammalian subjects, and are preferably mammalian. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and companion (or pet) birds (e.g., parrots and canaries), and birds in ovo.

The present invention is primarily concerned with the treatment of human subjects, but the invention can also be carried out on animal subjects, particularly mammalian subjects such as mice, rats, dogs, cats, livestock and horses for veterinary purposes, and for drug screening and drug development purposes.

Compounds and compositions of the present invention can be used to treat diseases, disorders or conditions treatable by the parent compound. By way of non-limiting example, compounds and compositions of the present invention can be used to treat diabetes, cancer, infections, cardiovascular diseases, respiratory disorders, sleeping disorders, neurological disorders, neurodegenerative diseases, gastrointestinal disorders, alopecia, musculoskeletal disorders, urogenital disorders, allergies, inflammation and pain.

Particular aspects of the present invention will now be described with reference to the following examples. It should be appreciated that these examples are for the purposes of illustrating aspects of the present invention, and do not limit the scope of the invention.

EXAMPLES

The following non-limiting examples are illustrative of the invention:

Synthesis of 4-(2-{2-[2-(2-Methoxy-ethoxy)-ethoxy]-ethoxy}-ethoxy)-phenol (Oligomer II)

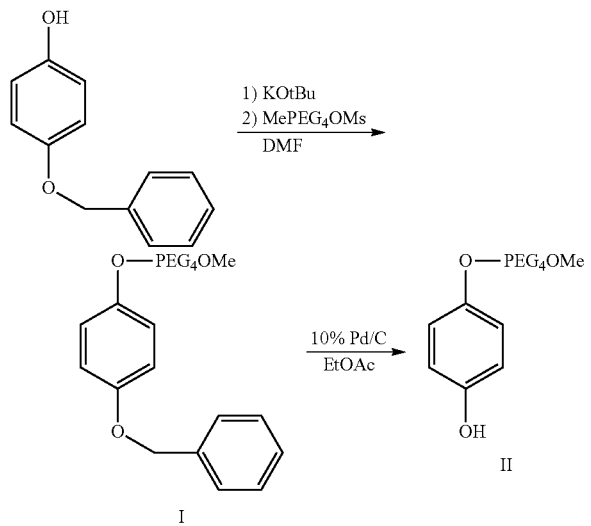

In a dry flask, 4-benzyloxyphenol (2.0 g, 10.0 mmol) was dissolved in 15 mL dry THF. Potassium tert-butoxide (0.446 g, 4.0 mmol) was added and the resulting mixture was stirred at room temperature. After one hour, a solution of $MPEG_4$ mesylate (0.945 g, 3.33 mmol) in 8 ml of dry THF was added. The entire mixture was stirred together overnight. The reaction was quenched with 10 mL MeOH and filtered through a short pad of Celite. The filtered reaction was concentrated to a thick brown oil. The crude product was purified via flash chromatography using EtOAc as the elutant to give 0.897 mg (23%) of $MPEG_4$ ether I.

Compound I (0.797 g, 2.04 mmol) was then dissolved in 50 mL EtOAc. An EtOAc slurry containing 0.081 g 10% Pd/C was added and the whole mixture was placed under a $H_2$ atmosphere and allowed to stir overnight at room temperature and 1 atmosphere of pressure. Additional catalyst was added until TLC (EtOAc) indicated that the reaction was complete. The mixture was then filtered through a short pad or Celite and the filtrate concentrated to give 0.483 g (79%) of the deprotected pegylated phenol, II. ESI MS: m/e 323.2 $(M+Na)^+$.

Synthesis of 4-[2-(2-{2-[2-(2-{2-[2-(2-Dodecyloxy-ethoxy)-ethoxy]-ethoxy}-ethoxy)-ethoxy]-ethoxy}-ethoxy)-ethoxy]-phenol (Oligomer V)

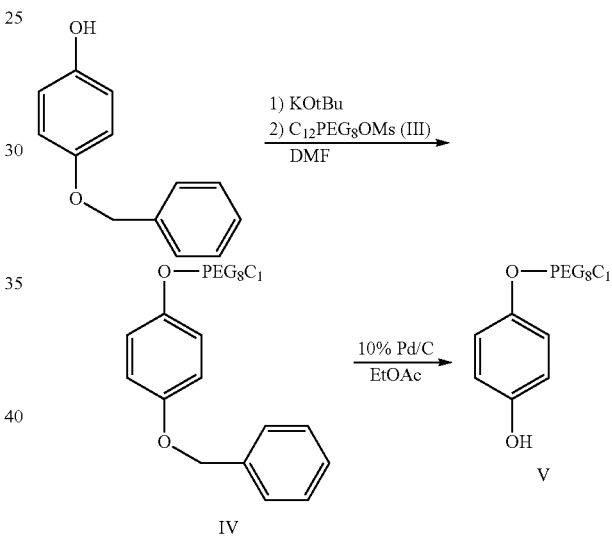

The mesylate of $C_{12}PEG_8OH$ was prepared by dissolving 10.0 g (18.6 mmol) of $C_{12}PEG_8OH$ in 60 mL of dry dichloromethane and cooling the resulting solution to 0° C. under $N_2$. To the cooled solution was added 3.1 mL (22.3 mmol) TEA and 1.72 mL (22.3 mmol) methanesulfonyl chloride. The reaction was allowed to proceed for 30 minutes at 0° C. and then allowed to warm to room temperature and stirred overnight. The reaction mixture was then diluted with another 50 mL dichloromethane and washed with saturated $NaHCO_3$ (2×20 mL) and water (3×20 mL). The organics were dried over $MgSO_4$, filtered and evaporated to dryness to give the mesylate, III. ESI MS: m/e 617.5 $(M+H)^+$, 639.4 $(M+Na)^+$.

The $C_{12}PEG_8$ mesylate, III, 8.97 g (16.65 mmol), in 60 mL dry DMF was added to a mixture of 10.0 g (49.9 mmol) 4-benzyloxyphenol and 2.24 g (20.0 mmol) potassium tert-butoxide that had been stirring in 80 mL dry DMF for one hour. The reaction was stirred at room temperature for three days and then quenched with 50 mL MeOH. The quenched reaction was filtered through a short pad of Celite and the filtrate was concentrated in vacuo. The crude product was purified by flash chromatography (gradient elution: 5/1 EtOAc/hexanes to EtOAc) to provide 4.59 g (38%) of IV as an orange oil. ESI MS: m/e 721.6 $(M+H)^+$, 743.6 $(M+Na)^+$.

Benzyl ether IV (1.00 g, 1.39 mmol) was dissolved in 30 mL EtOAc and a slurry of 100 mg of 10% Pd/C in EtOAc was added. The entire mixture was placed under $H_2$ and left stirring at room temperature. Additional catalyst was added until TLC indicated that all of the benzyl ether had been converted to phenol; then the reaction mixture was filtered through Celite and the filtrate evaporated to dryness to provide 0.854 g (98%) of V. ESI MS: m/e 653.5 $(M+Na)^+$.

Synthesis of 4-(2-{2-[2-(2-Methoxy-ethoxy)-ethoxy]-ethoxy}-ethoxymethyl)-phenol (Oligomer X)

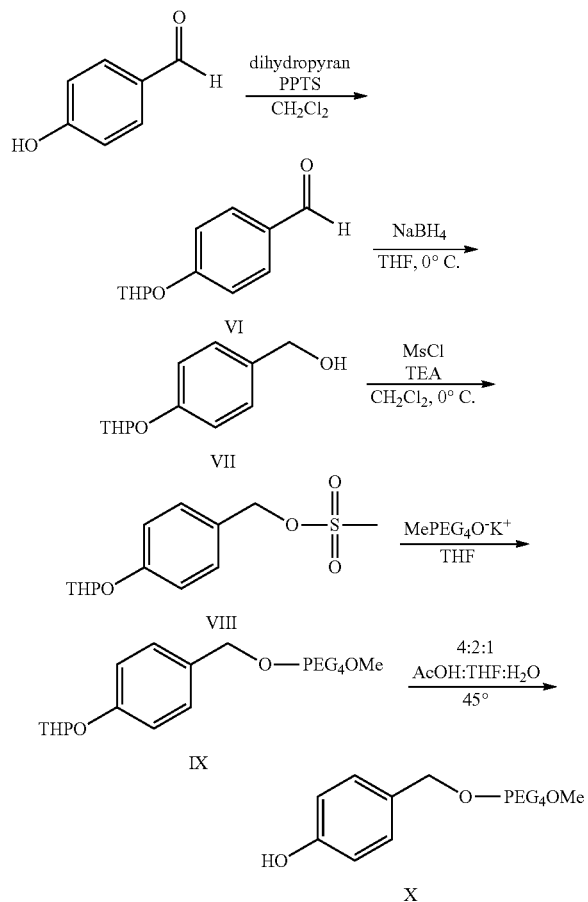

In a 500 mL round bottom flask was placed 5.00 g (40.9 mmol) 4-hydroxybenz-aldehyde, 200 mL dry $CH_2Cl_2$, 5.57 mL (61.4 mmol) dihydropyran, and 1.03 g (4.09 mmol) PPTS. The mixture was stirred at room temperature for 16 hours, then diluted with 100 mL more $CH_2Cl_2$ and washed with water (2×100 mL) and brine (1×100 mL). The organics were dried over $MgSO_4$, filtered and concentrated. The crude material was purified via flash chromatography (elutant: $CHCl_3$/5% MeOH) to afford 7.78 g (92%) of the THP protected phenol, VI.

Phenol VI (7.5 g, 36.4 mmol) was dissolved in 85 mL dry THF and cooled to 0° C. Sodium borohydride (1.37 g, 36.4 mmol) was added. After stirring for two hours at 0° C., the reaction was warmed to room temperature and allowed to stir overnight. The THF was stripped and the residue was taken up in 95 mL EtOAc and washed with water (2×45 mL). The organics were dried over $MgSO_4$, filtered and evaporated to dryness. Purification by flash chromatography (elutant: $CHCl_3$/4% MeOH) yielded 6.4 g (85%) of the benzyl alcohol, VII, as a clear oil.

The corresponding mesylate, VIII, was prepared by dissolving 6.00 g (28.8 mmol) of the benzyl alcohol in 36 mL dry $CH_2Cl_2$. The solution was cooled in an ice bath and then 4.82 mL (34.6 mmol) TEA and 2.68 mL (34.6 mmol) methanesulfonyl chloride was added. The reaction was stirred at 0° C. for thirty minutes and then at room temperature for an additional four hours. The reaction mixture was diluted with 20 mL $CH_2Cl_2$ and washed with saturated $NaHCO_3$ (2×20 mL) and water (3×20 mL). The organics were dried over $MgSO_4$, filtered and concentrated in vacuo to produce 5.77 g (70%) of VIII as an orange oil.

$MPEG_4OH$ (1.78 mL, 9.14 mmol) was dissolved in 50 mL dry THF and potassium tert-butoxide (2.16 g, 19.21 mmol) was added. The mixture was stirred at room temperature for one hour and then VIII (5.38 g, 19.2 mmol) in 20 mL THF was added and the whole mixture was stirred overnight at room temperature. The reaction was quenched with 50 mL MeOH and filtered through a short pad of Celite. The filtrate was concentrated in vacuo. Purification by flash chromatography (EtOAc) gave 1.28 g (17%) of the peylated benzyl alcohol, IX. ESI MS: m/e 421.1 $(M+Na)^+$.

In a solution containing 20 mL acetic acid, 10 mL THF, and 5 mL water, 1.0 g (2.51 mmol) of IX was dissolved. The mixture was warmed to 45° C. and stirred overnight. The reaction was diluted with 30 mL water, 20 mL saturated $NaHCO_3$ and 20 mL EtOAc. The organic layer was collected and the aqueous layer was extracted again with 20 mL EtOAc. The combined organic layers were dried over $MgSO_4$, filtered and evaporated to dryness to give 611 mg (77%) of oligomer X as a pale yellow oil. ESI MS: m/e 337.0 $(M+Na)^+$.

Synthesis of 3,4-Bis-(2-{2-[2-(2-methoxy-ethoxy)-ethoxy]-ethoxy}-ethoxy)-phenol (Oligomer XII)

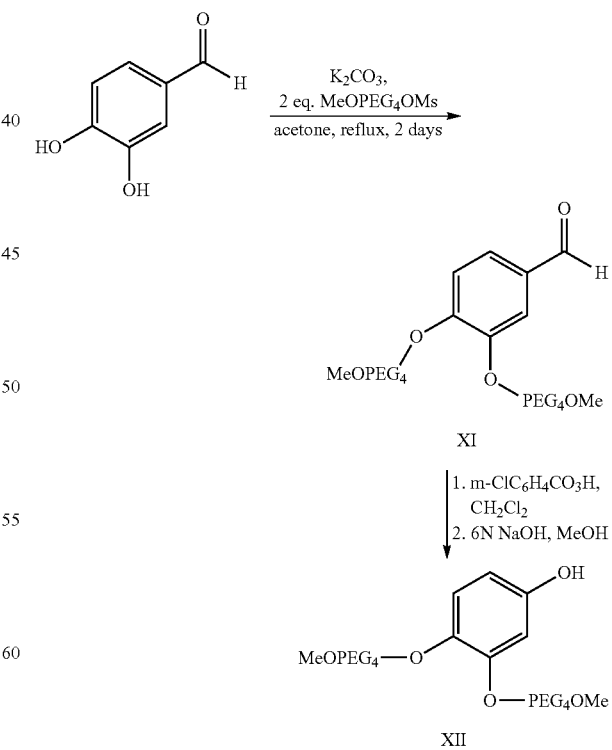

A mixture of 3,4-dihydroxybenzaldehyde (2.5 g, 18.1 mmol) and $K_2CO_3$ (5.25 g, 38.0 mmol) was suspended in 40 mL acetone. The mixture was heated to 56° C. and MPEG₄ mesylate (10.6 g, 37.1 mmol) was added. Over the course of the next three hours, a great deal of precipitate formed and another 20 mL of acetone was added. After three hours at 56° C., the reaction was cooled to 37° C. for 15 hours. TLC (EtOAc/10% MeOH) at this time indicated that there was still substantial unreacted and mono-PEG ether material remaining. Another 5.0 g (18.0 mmol) of mesylate in 20 mL acetone was added. The reaction mixture was heated to 56° C. for a further two days. The acetone was then stripped and the solid residue was taken up in a mixture of $CH_2Cl_2$ and water. The organics were washed with more water and brine, dried over $Na_2SO_4$, filtered and concentrated in vacuo. The crude product was purified via flash chromatography (gradient elution: EtOAc-EtOAc/10% MeOH) to give 2.78 g (30%) of the di-PEG ether benzaldehyde, XI.

The benzaldehyde XI (1.41 g, 2.72 mmol) was oxidized with mCPBA (0.73 g, 3.3 mmol) in dichloromethane (30 mL) overnight at room temperature. The reaction mixture was diluted with another 80 mL of dichloromethane and washed sequentially with saturated $NaHCO_3$, water and brine. The organics were dried over $Na_2SO_4$, filtered and concentrated in vacuo to a yellow oil which was then taken up in a mixture of 8 mL of MeOH and 1.0 mL of 6 N NaOH. The mixture turned purple immediately. After five minutes, the mixture was diluted with 50 mL of $CH_2Cl_2$ and washed once with 1 N HCl and then with water and brine. The organics were dried over $Na_2SO_4$, filtered and concentrated in vacuo. The resultant crude product was purified by flash chromatography (gradient elution: $CHCl_3$/2% MeOH—$CHCl_3$/5% MeOH) to give 0.624 g (45%) of XII as a dark purple oil. ESI MS: m/e 507 $(M+H)^+$, 529 $(M+Na)^+$, 545 $(M+K)^+$.

Synthesis of 4-Hydroxy-N-(2-{2-[2-(2-methoxy-ethoxy)-ethoxy]-ethoxy}-ethyl)-benzamide (Oligomer XV)

temperature then diluted in another 100 ml of $CH_2Cl_2$ and washed with water and brine. The organics were dried over $Na_2SO_4$, filtered and concentrated in vacuo. The crude product was purified by flash chromatography using $CH_2Cl_2$ as the elutant to give 1.91 g (64%) of the NHS ester of the benzoic acid.

This NHS ester, XIII, (0.78 g, 2.4 mmol) was dissolved in 20 mL $CH_2Cl_2$. TEA (0.354 mL, 0.257 g, 2.54 mmol) and MPEG₄ amine (0.403 g, 1.95 mmol) were added. The reaction was stirred at room temperature overnight. The crude reaction mixture was then diluted with another 20 mL of $CH_2Cl_2$ and washed with 0.5 N HCl (2×150 mL) water (2×150 mL) and brine (2×150 mL). The organics were dried over $Na_2SO_4$, filtered and concentrated in vacuo to an off-white solid that was purified by flash chromatography ($CHCl_3$/5% MeOH) to give 0.524 g (64%) of the desired amide, XIV.

The amide (0.524 g, 1.26 mmol) was dissolved in 40 mL of MeOH and added to 0.18 g of 5% Pd/C which had already been suspended in 60 mL EtOAc. The mixture was placed under a $H_2$ atmosphere and stirred at room temperature and 1 atm overnight. TLC ($CHCl_3$/15% MeOH) showed that all of the starting material had been consumed. The reaction was filtered through Celite to remove the catalyst. The Celite was washed with another 150 mL of EtOAc. The combined filtrate was concentrated in vacuo to give the 0.386 g (94%) of XV as a brown oil. FAB MS: m/e 328 $(M+H)^+$, 350 $(M+Na)^+$.

Synthesis of 5-Hydroxy-N,N'-bis-(2-{2-[2-(2-methoxy-ethoxy)-ethoxy}-ethoxy]-ethyl)-isophthalamide (Oligomer XX)

Benzyl chloride (5.20 ml, 45.0 mmol) and potassium carbonate (6.21 g, 45.0 mmol) were added to a solution of dimethyl-5-hydroxyisophthalate (7.0 g, 33 mmol) in 100 mL of acetone. Reaction was heated to reflux and let stir overnight. After confirmation by TLC the reaction was cooled to

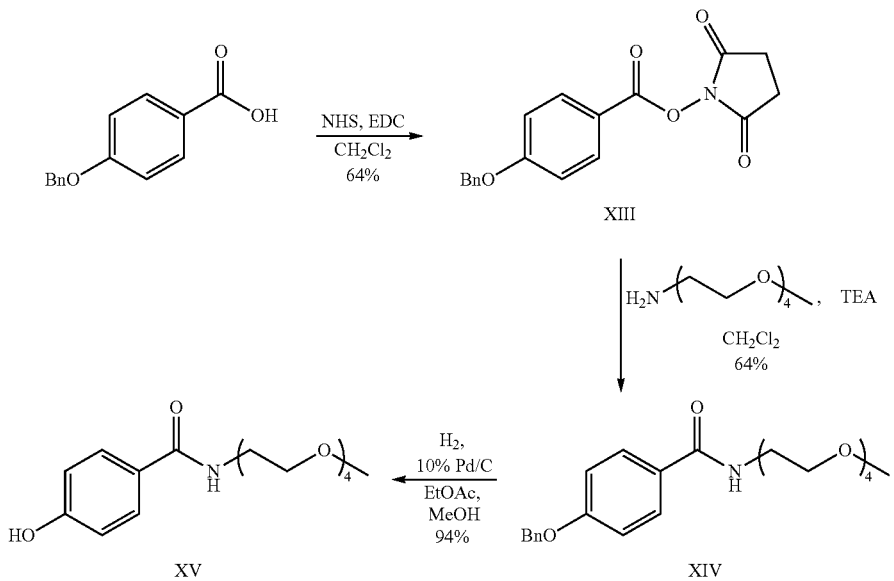

Compound XIII was prepared by mixing 3.0 g (13.1 mmol) of 4-benzyloxybenzoic acid with 50 mL of $CH_2Cl_2$. To this mixture was added 1.81 g (15.7 mmol) NHS and 3.01 g (15.7 mmol) EDC. The reaction was stirred overnight at room RT and concentrated in vacuo to yield the off-white solid product. Recrystallization from boiling cyclohexanes yielded 6.8 g (68%) of white crystalline XVI. ESI MS: m/e 301.1 $(M+H)^+$.

Compound XVI (6.7 g, 22 mmol) was added in portions to a stirring solution of 40 g KOH in 400 mL methanol. The reaction was refluxed for 2 hours. After cooling to room temperature, the mixture was acidified with 2N HCl to pH 2-3 causing the product to precipitate out. After filtering, XVII, a white solid, was obtained at 86% yield (5.15 g) ESI MS: m/e 271.0 (M–H)$^-$.

Compound XVII (2.00 g, 7.35 mmol) was dissolved in 80 mL dry $CH_2Cl_2$ and to this was added NHS (1.86 g, 16.2 mmol) and EDC (3.10 g, 16.2 mmol). After stirring overnight, the reaction mixture was diluted with 40 mL $CH_2Cl_2$ and washed with water (2×70 mL) and brine (2×70 mL). Organics were dried over $Na_2SO_4$ and concentrated to yield 3.05 g (90%) of white solid XVIII.

MPEG$_4$ amine (910 mg, 4.39 mmol) and TEA (0.611 mL, 4.39 mmol) were dissolved in 30 mL $CH_2Cl_2$ and let stir. Compound XVIII (682 mg, 1.46 mmol) was dissolved in 10 mL $CH_2Cl_2$ and added to the reaction. After stirring overnight, the reaction mixture was diluted with $CH_2Cl_2$ and washed with 1N HCl, water and brine (2×50 mL each). Organics were dried over $Na_2SO_4$ and concentrated to yield a yellow slurry. After purification by flash column chromatography ($CHCl_3$/MeOH 10/1) this gave 488 mg (51%) of XIX as a thick yellow oil. ESI MS: m/e 651.3 (M+H)$^+$.

Compound XIX (930 mg, 1.43 mmol) was dissolved in 80 mL EtOAc. Palladium on activated charcoal (10%) was then added (100 mg approximately) and the solution was stirred under $H_2$ overnight. The catalyst was removed by filtration through Celite and the filtrate was evaporated to yield 630 mg (80%) of white solid XX. ESI MS: m/e 561.3 (M+H)$^+$.

Synthesis of 3-(4-Hydroxy-phenyl)-2-(2-{2-[2-(2-methoxy-ethoxy)-ethoxy]-ethoxy}-ethoxycarbony-lamino)-propionic acid methyl ester (Oligomer XXII)

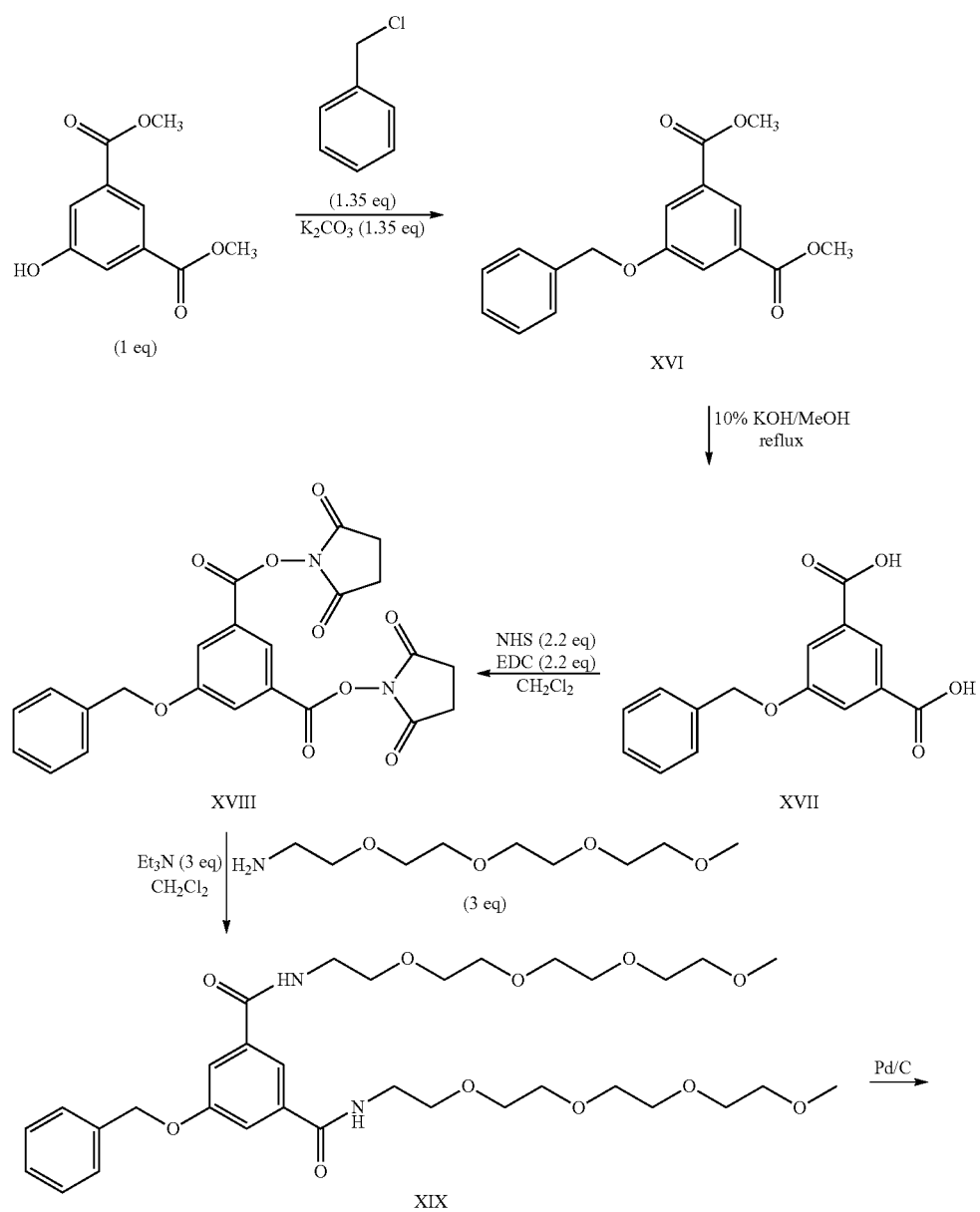

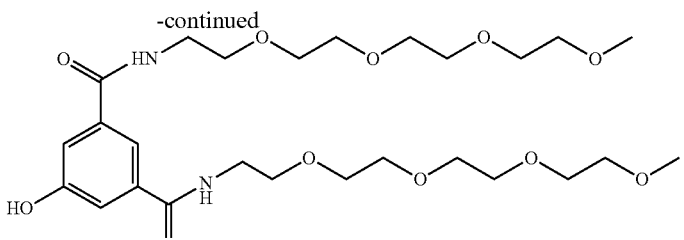

XIX

Tetraethylene glycol mono methyl ether (MPEG₄OH 4.00 g, 19.2 mmol) was dissolved in acetonitrile (40 mL) and disuccinimidyl carbonate (DSC, 5.44 g, 21.2 mmol) was added. Then triethylamine (4.00 mL, 28.8 mmol) was added dropwise and after 10 min the reaction mixture became clear. The reaction was stirred overnight at RT. After stirring for ~16 h, the crude reaction was evaporated to dryness and then dissolved in sat. NaHCO₃ (150 mL), washed with ethyl acetate (2×150 mL), dried over MgSO₄, and evaporated to dryness. Column chromatography (silica, EtOAc/MeOH, 10:1) afforded the oil XXI (4.04 g, 60% yield). ESI MS: m/e 372.1 (M+Na)⁺.

Tyrosine methyl ester (2.26 g, 12.5 mmol) and XXI were dissolved in CH₂Cl₂ (40 mL) and triethylamine was added (3.8 mL, 27 mmol). The reaction was stirred at room temperature overnight. After stirring for 18 hours, the crude reaction was diluted to 150 mL with CH₂Cl₂, washed H₂O (150 mL), sat NaHCO₃ (150 mL), 1 N HCl (150 mL), dried MgSO₄, and evaporated to dryness. Column chromatography (silica, EtOAc/MeOH, 25:1) afforded the oil XXII (3.51 g, 72%). ESI MS: m/e 430.1 (M+H)⁺, 452.2 (M+Na)⁺.

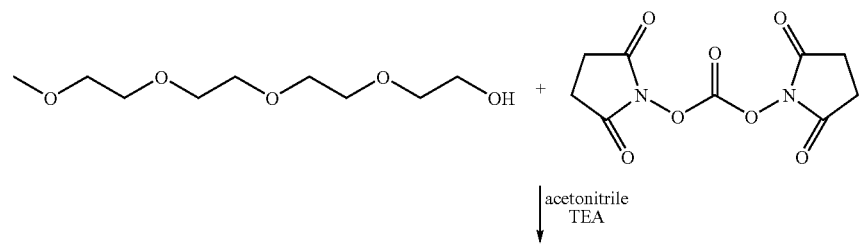

acetonitrile
TEA

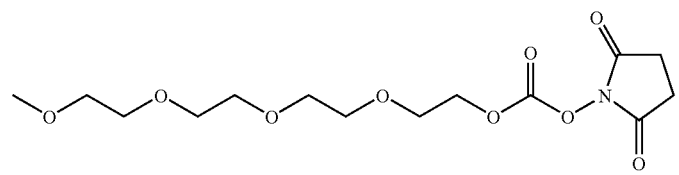

XXI

+

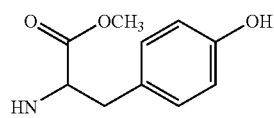

CH₂Cl₂
TEA

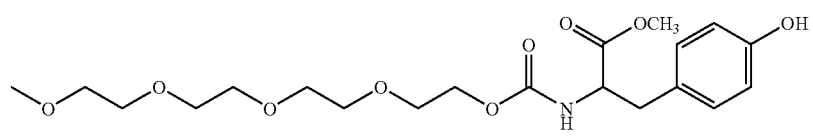

XXII

Synthesis of 2-[2-(2-Dodecyloxy-ethoxy)-ethoxycarbonylamino]-3-(4-hydroxy-phenyl)-propionic acid methyl ester (Oligomer XXIV)

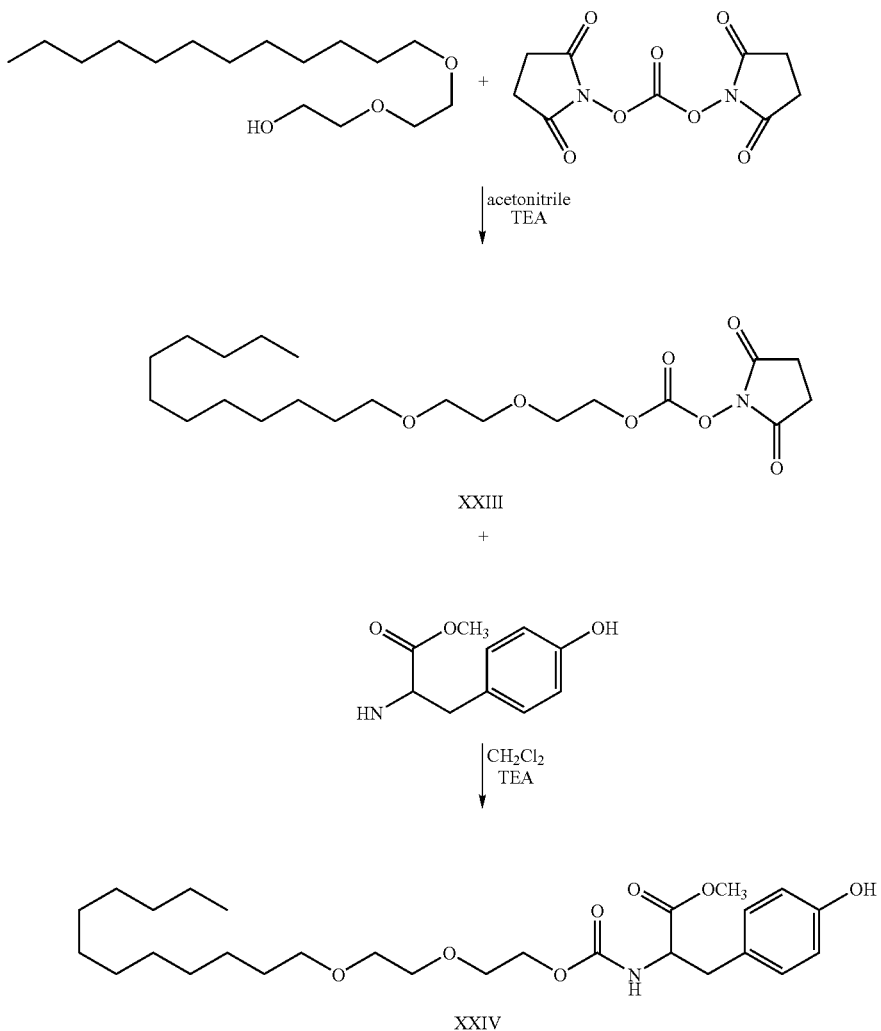

Oligomer XXIV was prepared in an analogous manner to that described above for Oligomer XXII. Diethylene glycol monododecyl ether (2.712 g, 9.88 mmol) was dissolved in 100 mL dry acetonitrile. Triethylamine (2.06 mL, 14.8 mmol) and DSC (3.80 g, 14.8 mmol) were added. After stirring for 18 hours at room temperature under an inert atmosphere, the reaction mixture was concentrated in vacuo. The residual oil was taken up in concentrated sodium bicarbonate solution and extracted with EtOAc (2×200 mL). The combined EtOAc layers were washed with water (2×100 mL) and brine (2×100 mL). The organics were dried over $Na_2SO_4$, filtered and evaporated to dryness to give 3.58 g (87%) of XXIII.

Tyrosine methyl ester (1.23 g, 5.30 mmol) was dissolved in 60 mL dry $CH_2Cl_2$. To the solution was added 0.738 mL (5.30 mmol) triethylamine. Compound XXIII (2.00 g, 4.80 mmol) was dissolved in 35 mL $CH_2Cl_2$ and added to the tyrosine methyl ester solution. After 17 hours at room temperature, the reaction mixture was worked up as described for compound XXII above. The crude product was purified by flash chromatography (silica, EtOAc/hexanes 1:1) to give 1.529 g (65%) of oligomer XXIV as a clear oil. ESI MS: m/e 495.4 $(M+H)^+$, 518.3 $(M+Na)^+$.

Synthesis of (4-Hydroxy-phenyl)-carbamic acid 2-{2-[2-(2-methoxy-ethoxy)-ethoxy]-ethoxy}-ethyl ester (Oligmer XXV)

4-Aminophenol (250 mg, 2.29 mmol) was dissolved in 20 mL THF. TEA (0.479 mL, 3.43 mmol) was added, followed by a solution of XXI (960 mg, 2.75 mmol) in 5 mL THF. The reaction was let stir overnight at room temperature. The reaction mixture was concentrated in vacuo to a thick yellow crude oil. After purification by flash column chromatography (silica, EtOAc) this gave 692 mg (88%) of XXV as a yellow oil. ESI MS: m/e 344.2 $(M+H)^+$.

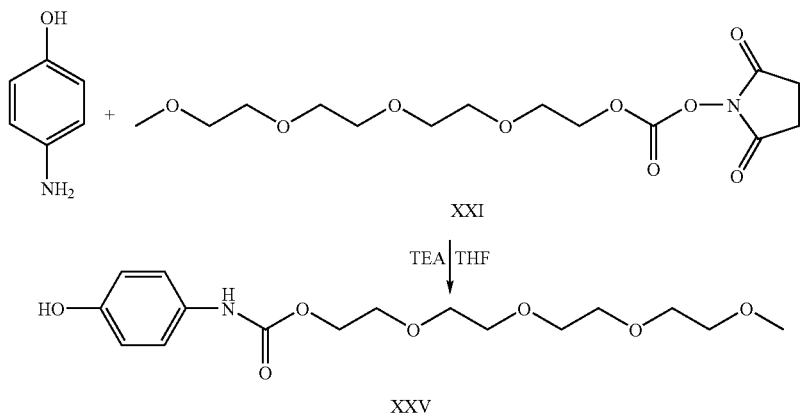

Synthesis of 4-{2-[2-(2-{2-[2-(2-Hexyloxy-ethoxy)-ethoxy]-ethoxy}-ethoxy)-ethoxy]-ethoxy}-phenol (Oligomer XXX)

The mesylate of 1-hexanol, XXVI, was prepared from 24.57 mL (195.8 mmol) of the alcohol dissolved in 80 mL dry dichloromethane. The solution was cooled to 0° C. and placed under an $N_2$ atmosphere. To the solution was added 32.74 mL (234.9 mmol) TEA. Methanesulfonyl chloride (18.18 mL, 234.9 mmol) was added dropwise. After thirty minutes at 0° C., the solution was allowed to warm to room temperature and let stir for three days. The mixture was diluted with 40 mL dichloromethane and washed with saturated $NaHCO_3$ (2×30 mL) and water (2×30 mL). The organics were dried over $MgSO_4$, filtered and concentrated in vacuo to 34.0 g (96%) of XXVI.

In 180 mL dry THF, 31.32 g (110.9 mmol) $PEG_6$ diol was dissolved. The solution was cooled to 0° C. Potassium tert-butoxide (12.45 g, 110.9 mmol) was added little by little and the entire mixture was stirred for one hour. XXVI (10.0 g, 55.5 mmol) was dissolved in 30 mL THF and added to the PEG solution. Following the addition of the mesylate, the reaction was kept at 0° C. for thirty minutes and then allowed to warm to room temperature and stirred overnight. The reaction was quenched with MeOH and filtered through Celite. The Celite was washed with dichloromethane and the combined filtrated was concentrated in vacuo. The concentrated residue was taken up in dichloromethane and washed with water several times. The organics were dried over $MgSO_4$, filtered and evaporated. The crude product was purified by flash chromatography (silica, EtOAc) to afford 4.66 g (23%) mono-hexyl $PEG_6$, XXVII. ESI MS: m/e 367.14 $(M+H)^+$, 389.08 $(M+Na)^+$, 405.06 $(M+K)^+$.

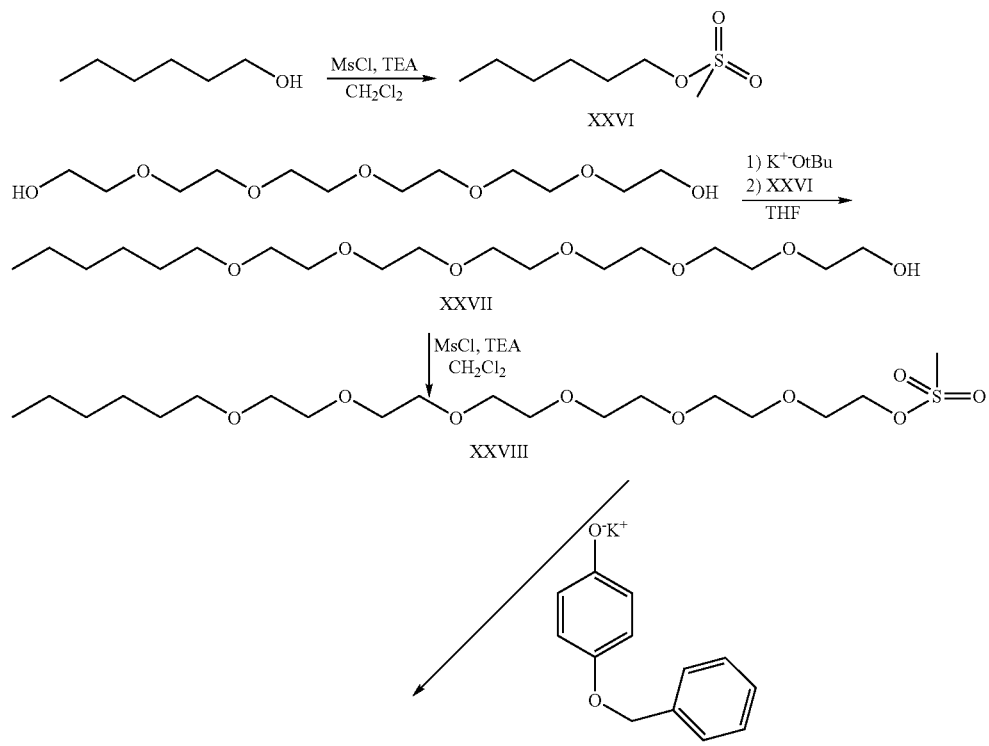

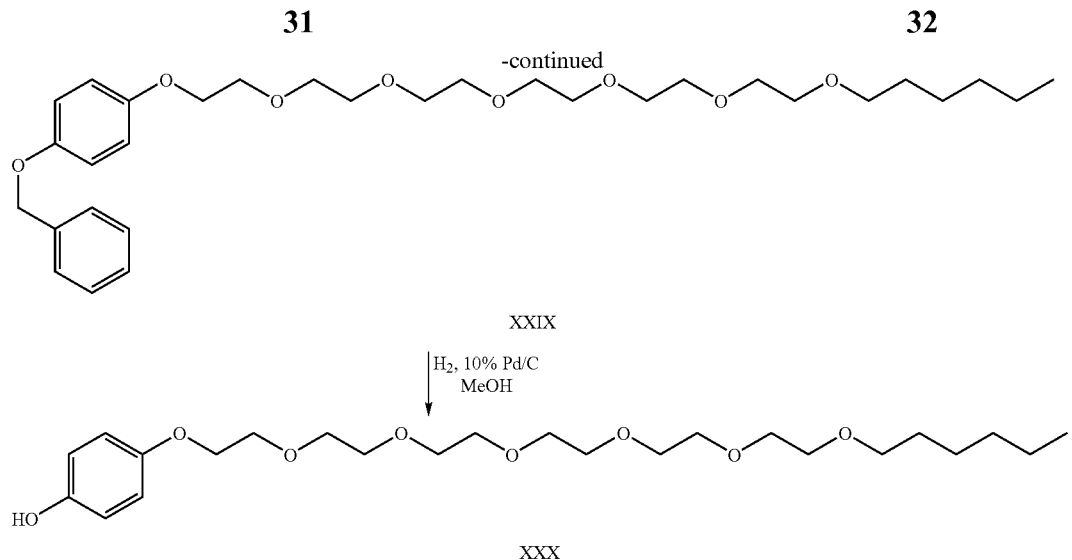

XXIX

↓ H₂, 10% Pd/C
   MeOH

XXX

To make the mesylate of the hexyl PEG alcohol, 17.00 g (46.5 mmol) of XXVII was dissolved in 70 mL dry $CH_2Cl_2$, cooled to 0° C., and placed under $N_2$. Triethylamine (7.78 mL, 55.8 mmol) was added and then methanesulfonyl chloride (4.32 mL, 55.8 mmol) was added dropwise. After thirty minutes at 0° C., the mixture was allowed to come to room temperature and then stirred overnight. The reaction mixture was diluted with more $CH_2Cl_2$ and washed with saturated $NaHCO_3$ and water. The organics were dried over $MgSO_4$, filtered and concentrated in vacuo to give 18.7 g (90%) of XXVIII. ESI MS: m/e 467.0 (M+Na)⁺.

In 50 mL THF, 5.00 g (25.0 mmol) 4-benzyloxyphenol was dissolved under $N_2$. Potassium tert-butoxide (1.12 g, 9.98 mmol) was added and the resulting mixture was stirred at room temperature for one hour. A solution of 1.12 g (9.98 mmol) of XXVIII in 20 mL THF was added to the benzyloxyphenol mixture, and the entire solution was stirred overnight at room temperature. The reaction was quenched with methanol and filtered through Celite. The filtrate was concentrated and purified by flash chromatography (silica, EtOAc/hexanes 5:2) to give 3.37 g (25%) of XXIX. ESI MS: m/e 571.05 (M+Na)⁺.

XXIX (3.37 g, 6.14 mmol) was dissolved in 90 mL MeOH. A slurry of 0.34 g 10% Pd/C in MeOH was added and the reaction was placed under $H_2$. After stirring at room temperature overnight, TLC (EtOAc) showed that all of the starting material was consumed. The reaction mixture was filtered through Celite and the filtrate was concentrated in vacuo to afford 2.54 g (90%) of oligomer XXX. ESI MS: m/e 459.19 (M+H)⁺, 480.98 (M+Na)⁺.

Synthesis of 4-(6-{2-[2-(2-{2-[2-(2-Methoxy-ethoxy)-ethoxy]-ethoxy}-ethoxy)-ethoxy]-ethoxy}-hexyloxy)-phenol (Oligomer XXXV)

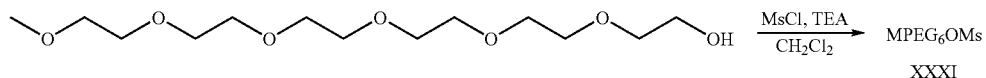

XXXI

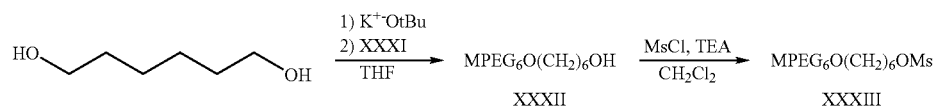

XXXII    XXXIII

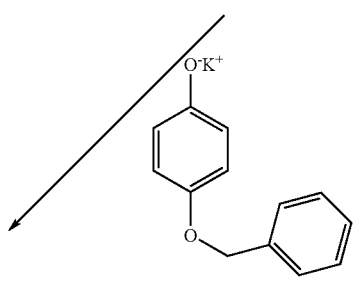

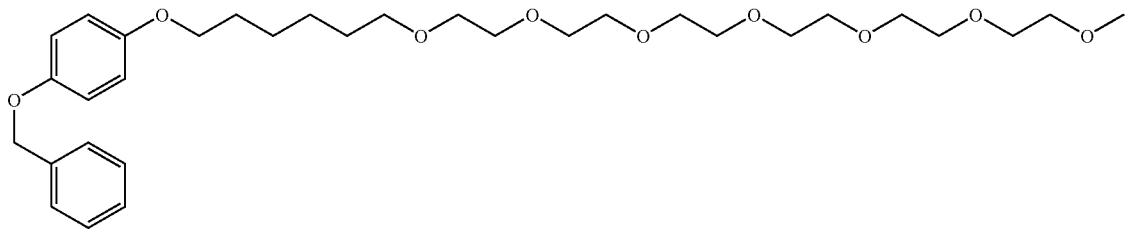

XXXIV

H$_2$, 10% Pd/C
MeOH

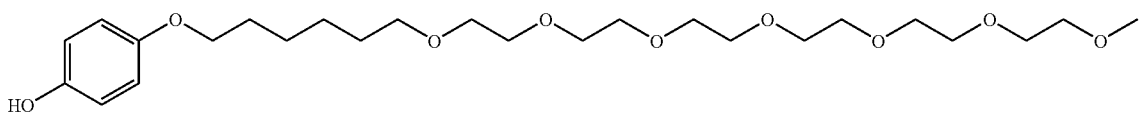

XXXV

MPEG$_6$ alcohol (10.0 g, 33.7 mmol) was dissolved in 40 mL dry CH$_2$Cl$_2$ and the resulting solution was cooled to 0° C. in an ice bath. TEA (5.64 mL, 40.5 mmol) was added and then 3.13 mL (40.5 mmol) methanesulfonyl chloride was added dropwise. The reaction was stirred for thirty minutes at 0° C. and then removed from the ice bath, allowed to come to room temperature and stirred overnight. The reaction mixture was diluted with more CH$_2$Cl$_2$ and washed with saturated NaHCO$_3$ and water. The organics were dried over MgSO$_4$, filtered and concentrated in vacuo to afford 12.4 g (98%) of MPEG$_6$ mesylate, XXXI.

A solution of 1,6-hexanediol was prepared from 6.311 g of the diol (53.41 mmol) and 180 mL of dry THF. The solution was cooled to 0° C. and placed under a N$_2$ atmosphere. Potassium tert-butoxide (5.996 g, 53.41 mmol) was added to the solution and the resulting mixture was stirred for one hour. XXXI (10.0 g, 26.7 mmol) in 30 mL THF was added to the mixture. All was stirred for a further 30 minutes at 0° C., then allowed to warm to room temperature and stirred overnight. The reaction mixture was filtered through Celite. The Celite was rinsed with CH$_2$Cl$_2$ and the combined filtrate was concentrated in vacuo. The residue was redissolved in CH$_2$Cl$_2$ and washed with water. The organics were dried over Na$_2$SO$_4$, filtered and evaporated to dryness. Purification by flash chromatography (silica, CHCl$_3$/10% MeOH). Some material was further purified by preparatory TLC (EtOAc/10% MeOH). Combined yield was 3.923 g (37%) of XXXII.

XXXII (3.923 g, 9.89 mmol) was dissolved in 16 mL dry CH$_2$Cl$_2$ and the resulting solution was cooled to 0° C. and placed under N$_2$. Triethylamine (1.65 mL, 11.9 mmol) was added and then 0.92 mL (11.9 mmol) methanesulfonyl chloride was added dropwise. The reaction was stirred at 0° C. for a further thirty minutes and then allowed to come to room temperature and stirred overnight. The reaction mixture was diluted with more CH$_2$Cl$_2$ and washed with saturated NaHCO$_3$ and water. The organics were dried over Mg$_2$SO$_4$, filtered and concentrated in vacuo to provide 4.25 g (91%) of mesylate XXXIII.

In a flask containing 50 mL dry THF, 5.001 g (24.97 mmol) of 4-benzyloxyphenol was dissolved. Potassium tert-butoxide (1.202 g, 9.989 mmol) was added and the resulting mixture was stirred for one hour at room temperature under an inert atmosphere. A solution of 3.950 g (8.324 mmol) of XXXIII in 20 mL THF was added. After a further 18 hours, the entire mixture was quenched with 10 mL MeOH and filtered through a short pad of Celite. The filtrate was concentrated in vacuo and the residue purified by flash chromatography (silica, EtOAc/MeOH 20:1) to provide 1.584 g (33%) of compound XXXIV. ESI MS: m/e 579.16 (M+H)$^+$, 601.14 (M+Na)$^+$.

Compound XXXIV (0.683 g, 1.18 mmol) was dissolved in 20 mL MeOH. To this solution was added a slurry of 136 mg of 5 Pd/C in MeOH. The entire mixture was placed under H$_2$ and stirred until TLC confirmed that all of the starting material had been consumed. The mixture was then filtered through Celite and the filtrate was evaporated to dryness to yield 412 mg (71%) of XXXV. ESI MS: m/e 511.09 (M+Na)$^+$.

Synthesis of 1-(4-Hydroxyphenyl)-2-(2-{2-[2-(2-methoxy-ethoxy)-ethoxy]-ethoxy}-ethoxy)-ethanone (Oligomer XXXIX)

as 2,2-Dibromo-2-cyano-N,N-dimethylacetamide or NBS to produce compound XXXVII. The bromide can then be displaced with the oxyanion of a PEG compound, such as MPEG$_4$OH. Deprotection of the phenolic group (in this case

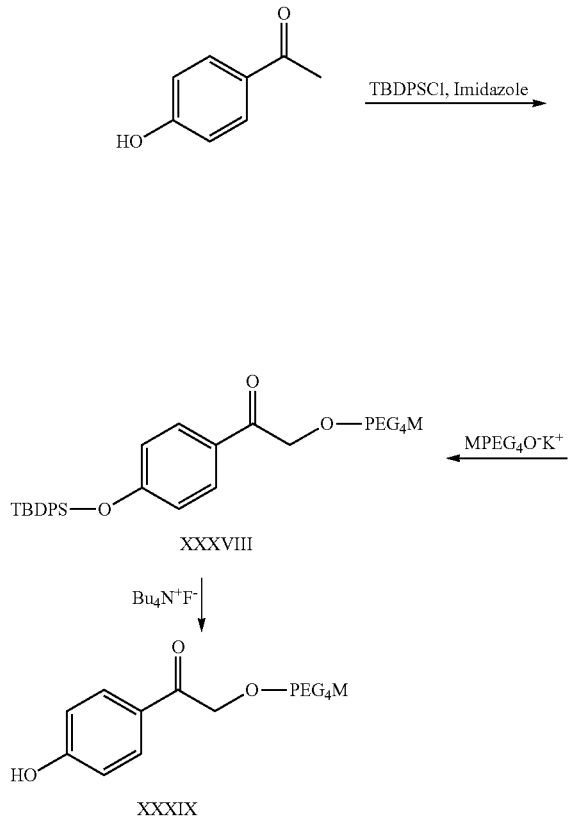

Compound XXXIX could be synthesized by protecting the phenolic moiety of 4-hydroxyacetophenone with a nucleophilically stable protecting group such as tert-butyldiphenylsilyl ether (TBDPS). The protected compound, XXXVI, can then be mono-brominated using a bromination reagent such tetra-butyl ammonium fluoride would remove the TBDPS ether) then gives the desired oligomer, XXXIX. Synthesis of 1-(4-Hydroxyphenyl)-4-(2-{2-[2-(2-methoxy-ethoxy)-ethoxy]-ethoxy}-ethoxy)-butan-1-one (Oligomer XXXXIV)

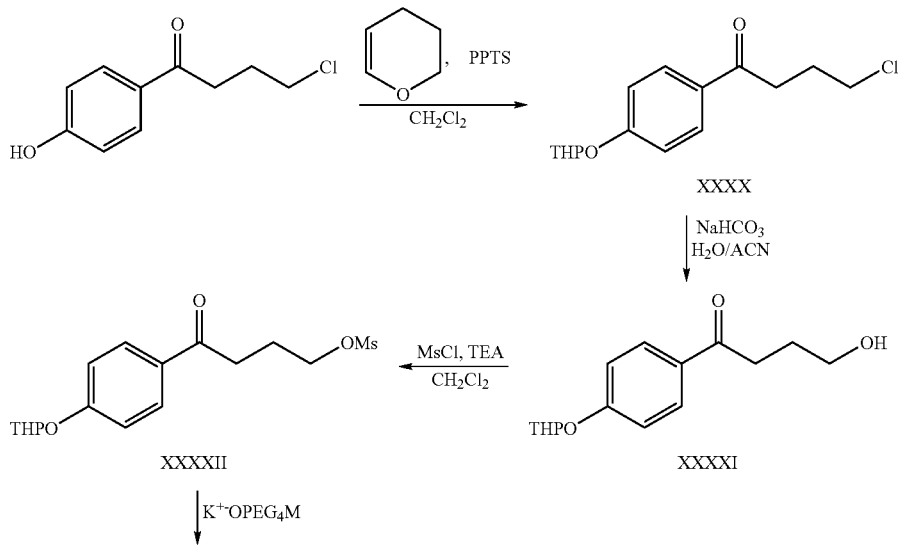

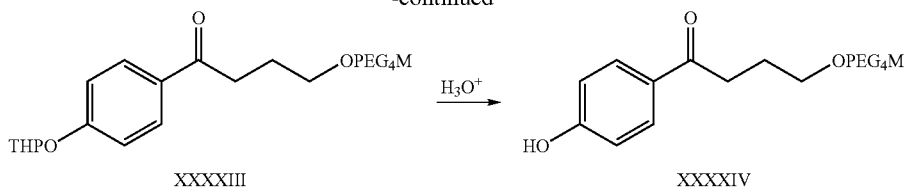

The phenolic group of (4-Hydroxyphenyl)-4'-chlorobutan-1-one can be protected as the THP ether with PPTS and dihydropyran. The chloride may then be converted to the alcohol using sodium bicarbonate while heating in a mixture of water and acetonitrile. The alcohol can be mesylated and then the mesylate displaced by the oxyanion of a PEG oligomer such as MPEG$_4$OH. Final deprotection of the THP group results in the title compound XXXXIV.

Activation of Oligomer XV

Oligomer XV (0.158 g, 0.482 mmol) was dissolved in 10 mL dry CH$_2$Cl$_2$. TEA (101 μL, 0.724 mmol) and p-nitrochloroformate (0.146 g, 0.724 mmol) were added. After four hours TLC (CHCl$_3$/15% MeOH) showed that all of the starting material had been consumed. The reaction mixture was diluted with another 15 mL CH$_2$Cl$_2$ and washed with cold water and cold brine. The organics were dried over Na$_2$SO$_4$, filtered and concentrated in vacuo. The crude product was purified via prep TLC with EtOAc as the elutant to yield 85 mg (36%) of the activated oligomer. ESI MS: m/e 493.2 (M+H)$^+$, 515.2 (M+Na)$^+$.

Activation of Oligomer XXX

The oligomer XXX (0.503 g, 1.09 mmol) was dissolved in 15 mL dry CH$_2$Cl$_2$. To this solution was added 0.23 mL (1.64 mmol) TEA and 0.329 g (1.64 mmol) p-nitro-phenylchloroformate. The reaction was stirred overnight at room temperature. The mixture was then diluted with a further 15 mL CH$_2$Cl$_2$ and washed with 15 mL 1 N HCl followed by 15 mL water. The organics were dried over MgSO$_4$, filtered and concentrated to dryness. The crude product was purified via flash chromatography (silica, gradient elution: 3/1 EtOAc/hexanes–EtOAc) to give 510 mg (75%) of the activated oligomer. ESI MS: m/e 624.13 (M+H)$^+$, 646.93 (M+Na)$^+$.

Prodrugs

Leu-Enk (Tyr-Gly-Gly-Phe-Leu) was chosen as a model peptide for conjugation. Leu Enk has only one primary amine available for conjugation. Prodrugs were made wherein insulin was the bioactive agent. Other examples employed include human insulin. The insulin prodrugs could have more than one oligomer, as insulin has more than one primary amine.

Conjugation of the Leu-Enk prodrugs

Polypeptide conjugates of the oligomers described above were synthesized as follows. LeuEnk (American Peptide Company) was dissolved in dry DMSO with two equivalents of TEA. A solution of the activated oligomer was prepared in dry THF. Oligomer solution was added to the peptide solution and the mixture was stirred gently at room temperature. Aliquots were removed and the reaction monitored by reverse-phase HPLC. The conjugates were purified by prep HPLC (using for example A C18 Vydac column, a water (0.1% TFA)/acetonitrile (0.1% TFA) gradient, monitoring by UV at 280 nm). Organic solvents were removed in vacuo and the remaining aqueous solution lyophilized to dryness. Insulin prodrug conjugates were synthesized via an analogous procedure.

Carboxylesterase Hydrolysis

Hydrolysis studies were performed with commercially available, purified carboxylesterase (in this case, rabbit liver carboxylesterase, an esterase that has been used to study the hydrolysis of the aryl carbamate of irinotecan, the small molecule prodrug of SN-38, and anti-cancer drug containing an aromatic hydroxyl group) in PBS buffer at 37° C. See Table 1.

TABLE 1

Carboxylesterase Hydrolysis in 0.05 M PBS buffer (pH 7.4)

| Conjugate | k* | $t_{1/2}$ **(hours) |
|---|---|---|
| Conjugate 1 (OPeg$_4$Me) | 0.0998 | 6.9 ± 0.1 |
| Conjugate 2 (OPeg$_8$C$_{12}$) | 0.0671 | 10.4 ± 0.9 |
| Conjugate 3 (PEG$_4$—OMe) | 0.2714 | 0.04 ± 0.17 |
| Conjugate 4 (MPeg$_4$, OCH$_3$, LeuEn) | 0.6000 | 1.3 ± 0.04 |

TABLE 1-continued

Carboxylesterase Hydrolysis in 0.05 M PBS buffer (pH 7.4)

| Conjugate | k* | $t_{1/2}$ **(hours) |
|---|---|---|
| 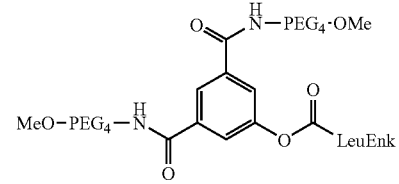 Conjugate 5 | 0.4434 | 0.03 ± 0.12 |
| 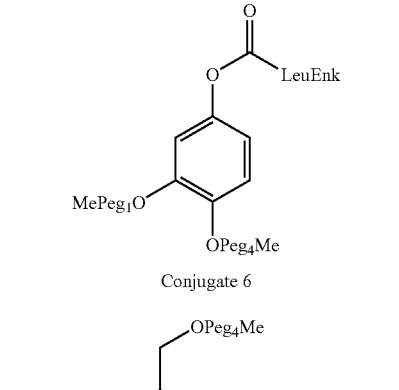 Conjugate 6 | 0.27 | 2.7 ± 0.2 |
|  Conjugate 7 | 0.5018 | 1.4 ± 0.1 |

*Value reported as average of three experiments
**Value reported as average of three experiments ± s. d.

Esterase Hydrolysis

Stock, or reference, solutions of hydrolyzable conjugates were first prepared at ~2 mg/mL in DMSO. Working solutions of the hydrolyzable conjugates were then prepared in triplicate (working solutions A). Fifty microliters of stock conjugate were added to 5.0 mL 50 mM PBS buffer.

A stock solution of carboxylesterase was prepared by adding ~2 mg esterase to 2.0 mL 50 mM PBS buffer. A working solution of carboxylesterase was prepared by diluting 50 uL of the stock solution with 5.0 mL 50 mM PBS buffer (working solution B).

Five hundred microliters of working solution B were then added to each working solution A (0.5 units enzyme and between 10-20 μM conjugate). The reaction mixtures were immediately vortexed and sampled for a time=0 analysis. The reaction solutions were incubated at 37° C. in a reciprocal waterbath shaker. At appropriate time intervals during incubation, 75 μL aliquots were taken and injected directly on HPLC for hydrolysis rate data. With each experiment, a new calibration curve for the particular conjugate was made.

Data for conjugates 1-7 is shown in FIGS. 1A-1G. The pseudo first-order rate constant, or "k", is obtained from the slope of the natural log of the concentration of the conjugate versus time curve. The half-life is then calculated from k.

Plasma Hydrolysis

Figure 2A:
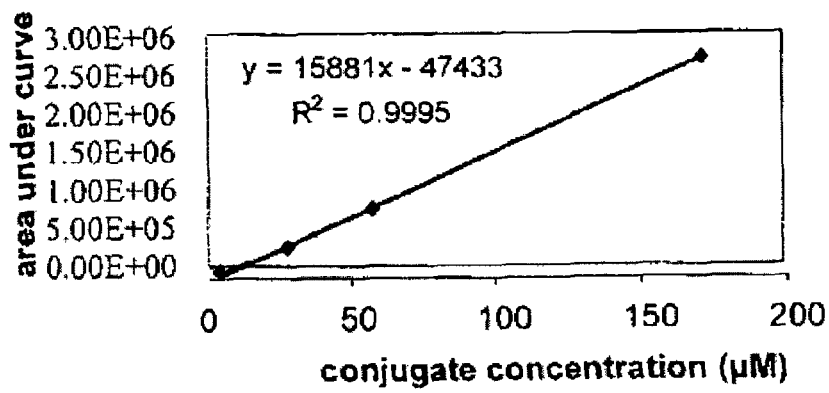
FIGS. 2A-B illustrate graphs depicting a standard curve for the determination of Conjugate 1 concentration (μM) for ex vivo rat plasma studies (FIG. 2A) and a graph showing the ln Conjugate 1 conc. (μM) versus time (min.) in rat plasma at 37° C.
Figure 2B:
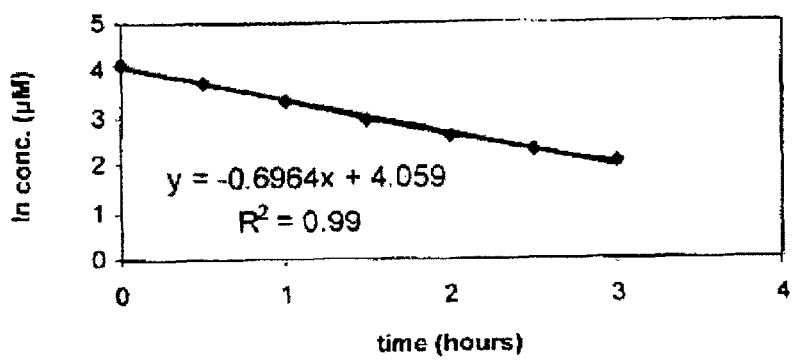

Experiments using rat plasma were conducted in similar fashion to the esterase hydrolysis experiments. A stock, or reference, solution of each conjugate was made that was ~15 mg/mL in DMSO. Two hundred microliters of stock were added to 800 μL 50 mM PBS buffer. Fifty microliters of this latter solution were added to 950 μL rat plasma and placed at 37° C. in a reciprocal waterbath shaker. At the appropriate time intervals, a 50 μl, aliquot was taken, added to 100 μl, ACN, and vigorously vortexed for 1 minute. The sample was centrifuged at 10,000 rpm for 5 minutes and 50 μL, of supernatant was then injected for HPLC analysis. A calibration curve for measuring the concentration of each conjugate was made. The calibration curve for Conjugate 1 is shown in FIG. 2A. The hydrolysis curve for Conjugate 1 in rat plasma at 37° C. is shown in FIG. 2B.

TABLE 2

Ex Vivo Hydrolysis in Rat Plasma at 37° C.

| Conjugate | k* | $t_{1/2}$ **(min) |
|---|---|---|
| 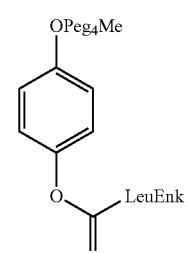 Conjugate 1 | 0.7625 | 54.75 ± 4.34 |
|  Conjugate 2 | 0.0050 | 139.63 ± 4.34 |
| 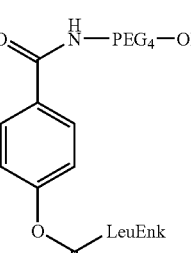 Conjugate 3 | | ~Immediate Hydrolysis |

TABLE 2-continued

Ex Vivo Hydrolysis in Rat Plasma at 37° C.

| Conjugate | k* | $t_{1/2}$**(min) |
|---|---|---|
| Conjugate 8 (HN-PEG$_4$-OMe, phenyl, O-C(=O)-LeuEnk) | 0.0487 | 15.03 ± 4.63 |
| Conjugate 5 (MeO-PEG$_4$-NH-C(=O), C(=O)-NH-PEG$_4$-OMe, phenyl, O-C(=O)-LeuEnk) | | ~Immediate Hydrolysis |
| Conjugate 6 (MePeg$_2$O, OPeg$_4$Me, phenyl, O-C(=O)-LeuEnk) | 0.0335 | 21.24 ± 4.00 |
| Conjugate 7 (OPeg$_4$Me, benzyl, O-C(=O)-LeuEnk) | 0.0075 | 1.62 ± 0.44 |

*Value reported as average of three experiments
**Value reported as average of three experiments ± s.d.

TABLE 3

Ex Vivo Hydrolysis in Rat Plasma at 37° C.

| Conjugate | Site# | k* | $t_{1/2}$**(hours) |
|---|---|---|---|
| Conjugate 9$_{a-d}$ (OC$_6$Peg$_6$Me, phenyl, O-C(=O)-insulin) | mono 1 | 0.0744 | 9.3 ± 0.5 |
| | mono 2 | 0.0224 | 31.0 ± 1.5 |
| | mono 3 | 0.0374 | 18.9 ± 2.9 |
| | di | 0.0764 | 9.1 ± 0.3 |
| Conjugate 10$_{a-c}$ (OPeg$_6$C$_6$, phenyl, O-C(=O)-insulin) | mono 1 | 0.0235 | 30.5 ± 6.4 |
| | mono 2 | 0.0528 | 13.1 ± 0.6 |
| | di | 0.1124 | 6.2 ± 0.1 |

TABLE 3-continued

Ex Vivo Hydrolysis in Rat Plasma at 37° C.

| Conjugate | Site# | k* | $t_{1/2}$** (hours) |
|---|---|---|---|
| Conjugate 11$_{a-c}$ | mono 1 | 0.0260 | 27.4 ± 5.4 |
| | mono 2 | 0.0562 | 12.4 ± 1.1 |
| | di | 0.0711 | 9.9 ± 1.2 |
| Conjugate 12*** | mono 1 | 0.351 | <0.25 (not stable in buffer) |
| | mono 2 | 0.0453 | 19.8 ± 0.3 |
| | di | | 15.7 ± 3.1 |
| Conjugate 13$_{a-b}$ | mono 1 | 0.1305 | 5.9 ± 2.4 |
| | mono 2 | 0.0716 | 10.5 ± 3.8 |

*Value reported as average of three experiments
**Value reported as average of three experiments ± s. d.
Numbered in order elution from column
***Insulin conjugated at other sites with the same oligomer showed rapid hydrolysis of the methyl ester, but only slow (t1/2 > 15 hr.) hydrolysis of the aryl carbamate

CONCLUSION

The invention has been described with respect to its various embodiments described herein. The invention may be embodied in different forms and should not be construed as limited to the specific embodiments set forth herein. Rather, these embodiments are provided so that this disclosure will be thorough and complete, and will fully convey the scope of the invention to those skilled in the art. Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

We claim:

1. An activated compound where an activated moiety is attached to the hydroxyl group and wherein the activated moiety is selected from the group consisting of chloroformate, NHS carbonate, disuccinimidyl carbonate (DSC), phosgene and paranitrophenyl carbonate, wherein the activated compound has a formula selected from the group consisting of:

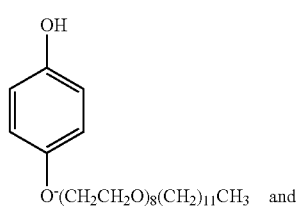

(Compound 2)

and

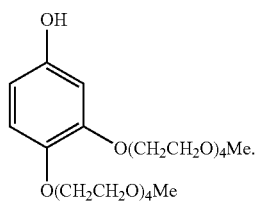

* * * * *